US009359279B2

(12) United States Patent
Shih et al.

(10) Patent No.: US 9,359,279 B2
(45) Date of Patent: *Jun. 7, 2016

(54) TREATMENT OF CANCER, INFLAMMATORY DISEASE, AND AUTOIMMUNE DISEASE

(71) Applicant: AndroScience Corporation, Solana Beach, CA (US)

(72) Inventors: Charles C-Y Shih, San Diego, CA (US); Toshio Kitamura, Tokyo (JP); Qian Shi, Chapel Hill, NC (US); Toshiyuki Kawashima, Solana Beach, CA (US); Hui-Kang Wang, San Diego, CA (US)

(73) Assignee: Allianz Pharmascience Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/471,539

(22) Filed: Aug. 28, 2014

(65) Prior Publication Data

US 2014/0371177 A1    Dec. 18, 2014

Related U.S. Application Data

(63) Continuation of application No. 13/210,728, filed on Aug. 16, 2011, now Pat. No. 8,822,732.

(60) Provisional application No. 61/375,534, filed on Aug. 20, 2010.

(51) Int. Cl.

| | | |
|---|---|---|
| C07D 211/20 | (2006.01) |
| C07C 49/00 | (2006.01) |
| C07C 307/00 | (2006.01) |
| C07C 309/00 | (2006.01) |
| C07C 303/00 | (2006.01) |
| C07C 311/00 | (2006.01) |
| C07F 9/02 | (2006.01) |
| C07C 233/00 | (2006.01) |
| C07C 235/00 | (2006.01) |
| C07C 237/00 | (2006.01) |
| C07C 239/00 | (2006.01) |
| C07C 213/00 | (2006.01) |
| C07C 215/00 | (2006.01) |
| C07C 217/00 | (2006.01) |
| A61K 31/66 | (2006.01) |
| A61K 31/12 | (2006.01) |
| A61K 31/255 | (2006.01) |
| A61K 31/445 | (2006.01) |
| A61K 31/165 | (2006.01) |
| A61K 31/135 | (2006.01) |
| A61K 31/535 | (2006.01) |
| C07C 49/248 | (2006.01) |
| C07C 49/235 | (2006.01) |
| C07C 49/255 | (2006.01) |
| C07C 69/16 | (2006.01) |
| C07C 217/22 | (2006.01) |
| C07C 235/82 | (2006.01) |
| C07C 307/02 | (2006.01) |
| C07C 309/65 | (2006.01) |
| C07C 309/66 | (2006.01) |
| C07C 309/73 | (2006.01) |
| C07C 317/24 | (2006.01) |
| C07D 213/68 | (2006.01) |
| C07D 295/112 | (2006.01) |
| C07F 9/12 | (2006.01) |

(Continued)

(52) U.S. Cl.
CPC ............ *C07C 49/248* (2013.01); *C07C 49/235* (2013.01); *C07C 49/255* (2013.01); *C07C 69/16* (2013.01); *C07C 217/22* (2013.01); *C07C 217/60* (2013.01); *C07C 235/82* (2013.01); *C07C 307/02* (2013.01); *C07C 309/65* (2013.01); *C07C 309/66* (2013.01); *C07C 309/73* (2013.01); *C07C 317/24* (2013.01); *C07D 213/68* (2013.01); *C07D 295/112* (2013.01); *C07D 295/13* (2013.01); *C07F 9/06* (2013.01); *C07F 9/09* (2013.01); *C07F 9/12* (2013.01); *C07F 9/32* (2013.01); *C07F 9/3282* (2013.01); *C07C 2101/14* (2013.01); *C07C 2101/16* (2013.01)

(58) Field of Classification Search
None
See application file for complete search history.

(56) References Cited

U.S. PATENT DOCUMENTS

| | | | |
|---|---|---|---|
| 8,822,732 B2 * | 9/2014 | Shih | ...................... C07C 49/235 568/300 |
| 2006/0276536 A1 | 12/2006 | Vander Jagt et al. | |

(Continued)

FOREIGN PATENT DOCUMENTS

| | | |
|---|---|---|
| JP | 05509078 A | 12/1993 |
| JP | 2008029977 | 2/2008 |
| WO | WO-2007000998 A1 | 1/2007 |

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
Lagisetty et al "CLEFMA—An Anti-Proliferative Curcuminoid Prom Structure-Activity Relationship Studies on 3,5-Bis(Benzylidene)-4-Piperidones" Bioorganic & Medicinal Chemistry, vol. 18, pp. 6109-6120. 2010.

(Continued)

*Primary Examiner* — Janet L Andres
*Assistant Examiner* — Ben S Michelson
(74) *Attorney, Agent, or Firm* — Cesari and McKenna LLP

(57) ABSTRACT

A method of treating cancer, inflammatory disease, and autoimmune disease by administering to a subject in need thereof an effective amount of one or more 1,5-dipenylpenta-1,4-dien-3-one compounds. The compounds feature either or both of the phenyl rings being substituted with hydroxyl, diethyl(2-alkoxyethyl)amine, 1-(2-alkoxyethyl)piperidine, sulfonate, phosphinate, or phosphate.

19 Claims, No Drawings

(51) Int. Cl.
*C07F 9/32* (2006.01)
*C07C 217/60* (2006.01)
*C07D 295/13* (2006.01)
*C07F 9/06* (2006.01)
*C07F 9/09* (2006.01)

(56) References Cited

U.S. PATENT DOCUMENTS

2008/0234320 A1 9/2008 Snyder et al.
2010/0152493 A1 6/2010 Shibata et al.

OTHER PUBLICATIONS

Hu et al "Curcumin Derivatives Inhibit Testicular 17β-Hydroxysteroid Dehydrogenase 3" Bioorganic & Medicinal Chemistry Letters, vol. 20, pp. 2549-2551. 2010.
Pyman. "CXLII.—isoQuinoline Derivatives. Part I. Oxidation of Laudanosine." Journal of the Chemical Society, Transcations, vol. 95, pp. 1266-1275. 1909.
Adams et al. "Synthesis and Biological Evaluation of Novel Curcumin Analogs as Anti-Cancer and Anti-Angiogenesis Agents" Bioorganic & Medicinal Chemistry vol. 12, pp. 3871-3883. 2004.
Youssef et al. "Synthesis of Curcumin Analogues as Potential Antioxidant, Cancer Chemopreventive Agents" Arch. Pharm. Pharm. Med. Chem. vol. 337, pp. 42-54. 2004.
Dudkina et al. "Nanocomposites of NLO Chromophore-Modified Layered Silicates and Polypropylene" Journal of Polymer Science vol. 43, pp. 2493-2505. 2005.
Carey. "Organic Chemistry" Sixth Edition, pp. 2-10. 2006.
Qiu et al. "Synthesis and Evaluation of Curcumin Analogues as Potential Thioredoxin Reductase Inhibitors" Bioogranic & Medicinal Chemistry vol. 16, pp. 8035-8041. 2008.
Fuchs et al. "Structure-Activity Relationship Studies of Curcumin Analogues" Bioorganic & Medicinal Chemistry Letters vol. 19, pp. 2065-2069. 2009.
Liu et al. "Design, Synthesis and Antitumor Activity of Substituted Benzylidenecyclopentanone Derivatives" Chinese Journal of Medicinal Chemistry vol. 20, pp. 11-24. 2010.
Yadav et al. "Synthesis and Cytotoxic Potential of Heterocyclic Cyclohexanone Analogues of Curcumin" Bioorganic & Medicinal Chemistry vol. 18, pp. 6701-6707. 2010.
Yamakoshi et al. "Structure-Activity Relationship of C5-Curcuminoids and Synthesis of Their Molecular Probes Thereof" Bioorganic & Medicinal Chemistry vol. 18, pp. 1083-1092. 2010.
Yingxiang Liu et al: "Design, synthesis and antitumor activity of substituted (benzylidene)cyclopentanone derivatives", Chinese Journal of Medicinal Chemistry., vol. 20, No. 1, Feb. 1, 2010, CN, pp. 11-18.

* cited by examiner

TREATMENT OF CANCER, INFLAMMATORY DISEASE, AND AUTOIMMUNE DISEASE

CROSS REFERENCE TO RELATED APPLICATIONS

This application is a continuation of U.S. application Ser. No. 13/210,728, filed on Aug. 16, 2011, which claims the benefit U.S. Provisional Application No. 61/375,534, filed on Aug. 20, 2010. The contents of both applications are hereby incorporated by reference in their entirety.

BACKGROUND OF THE INVENTION

Signal Transducer and Activator of Transcription (STAT) proteins are transcription factors that mediate cellular responses to growth factors. These proteins are activated via tyrosine phosphorylation by growth factor receptor-associated tyrosine kinases. Activated STAT proteins promote cell survival and proliferation. It is now well established that persistent activation of STAT3 or STAT5 promotes cell growth, invasion, and metastasis of both solid and hematopoietic cancers. See, e.g., Expert Opin. Investig. Drugs, 2009, 18(1): 45-56.

In normal lymphoid cells, STAT proteins, e.g., STAT3, also mediate cellular responses to cytokines, such as interleukin-6 (IL-6), via cytokine receptor-associated Janus kinases (JAKs). See, e.g., Neoplasia 2008, 10: 287-297. IL-6 is abnormally elevated in patients suffering from hematopoietic cancers, inflammatory diseases, autoimmune diseases, and postmenopausal osteoporosis. Inhibiting cellular action of IL-6, e.g., by inducing STAT3 proteins degradation, has attributed to treatment of these diseases.

As such, compounds that deactivate STAT proteins can be used to treat various cancers, inflammatory diseases, and autoimmune diseases.

SUMMARY OF THE INVENTION

This invention is based on a discovery that a group of compounds having a backbone of 1,5-diphenyl-penta-1,4-dien-3-one deactivate STAT proteins.

One aspect of this invention relates to a compound of Formula (I):

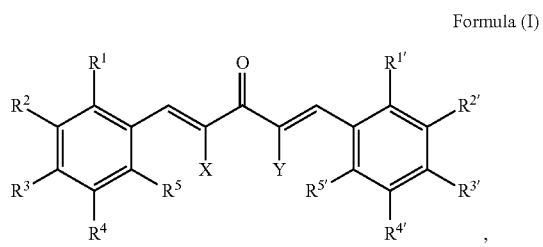

Formula (I)

wherein each of X and Y, independently, is H, alkyl, or halo, or X and Y together are
—$CH_2$—, —$(CH_2)_2$—, —$(CH_2)CR_aR_b(CH_2)$—, —$(CH_2)NR_a(CH_2)$—, or —$(CH_2)O(CH_2)$—, each of $R_a$ and $R_b$, independently, being H, alkyl, C(O)-alkyl, C(O)-cycloalkyl, C(O)—NH-alkyl, or C(O)—NH-cycloalkyl; and each of $R^1$, $R^2$, $R^3$, $R^4$, $R^5$, $R^{1'}$, $R^{2'}$, $R^{3'}$, $R^{4'}$, and $R^{5'}$, independently, is H, alkyl (e.g., alkyl substituted with halo or $SO_2R_d$), halo, OH, $R_c$—O—, $R_dS(O)_2$—O—, or $(R_d)_2P(O)$—O—, $R_c$ being unsubstituted alkyl or alkyl substituted with halo, OH, alkoxy, amino, cycloalkyl, heterocycloalkyl, aryl, or heteroaryl, and $R_d$ being H, OH, alkyl, alkoxy, amino, or aryl; in which $R^1$ is different from $R^{1'}$ or $R^{5'}$, $R^2$ is different from $R^{2'}$ or $R^{4'}$, $R^3$ is different from $R^{3'}$, $R^4$ is different from $R^{2'}$ or $R^{4'}$, or $R^5$ is different from $R^{1'}$ or $R^{5'}$.

Referring to Formula (I), a subset of the compounds have one or more of the following features: $R^2$ is OH or $R^2$ is $R_dS(O)_2$—O—, or $(R_d)_2P(O)$—O— ($R_d$ is H, OH, alkyl, alkoxy, amino, or aryl, e.g., $R_d$ is ethyl); $R^{2'}$ is $R_c$—O— ($R_c$ is alkyl substituted with amino); each of X and Y is H or X and Y together are —$(CH_2)NR_a(CH_2)$—; and $R_a$ is C(O)—R, C(O)NRR', or alkyl substituted with cycloalkyl (each of R and R', independently, is alkyl or cycloalkyl).

Another aspect of this invention relates to a compound of Formula (II):

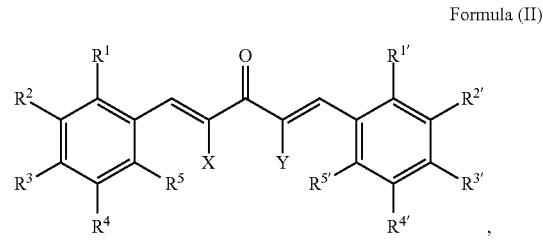

Formula (II)

wherein each of X and Y, independently, is H, alkyl, or halo, or X and Y together are
—$CH_2$—, —$(CH_2)_2$—, —$(CH_2)CR_aR_b(CH_2)$—, —$(CH_2)NR_a(CH_2)$—, or —$(CH_2)O(CH_2)$—, each of $R_a$ and $R_b$, independently, being H, alkyl, C(O)-alkyl, C(O)-cycloalkyl, C(O)—NH-alkyl, or C(O)—NH-cycloalkyl; and each of $R^1$, $R^2$, $R^3$, $R^4$, $R^5$, $R^{1'}$, $R^{2'}$, $R^{3'}$, $R^{4'}$, and $R^{5'}$, independently, is H, alkyl (e.g., alkyl substituted with halo or $SO_2R_d$), halo, OH, $R_c$—O—, $R_dS(O)_2$—O—, or $(R_d)_2P(O)$—O—, $R_c$ being unsubstituted alkyl or alkyl substituted with halo, OH, alkoxy, amino, cycloalkyl, heterocycloalkyl, aryl, or heteroaryl, and $R_d$ being H, OH, alkyl, aloxyl, amino, or aryl; in which at least one of $R^1$, $R^2$, $R^3$, $R^4$, $R^5$, $R^{1'}$, $R^{2'}$, $R^{3'}$, $R^{4'}$, and $R^{5'}$ is $R_dS(O)_2$—O—, $(R_d)_2P(O)$—O—, or $(R_dO)_2P(O)$—O—.

Referring to Formula (II), a subset of the compounds have one or more of the following features: each of X and Y is H; $R^2$ is $R_dS(O)_2$—O—, or $(R_d)_2P(O)$—O— ($R_d$ is H, OH, alkyl, alkoxy, amino, or aryl; e.g., $R_d$ is ethyl); $R^{2'}$ is R—O— (R is alkyl substituted with amino), or $R^{2'}$ is $R_dS(O)_2$—O—, or $(R_d)_2P(O)$—O— ($R_d$ is H, OH, alkyl, alkoxy, amino, or aryl, e.g., $R_d$ is ethyl); and one of $R^{1'}$, $R^{3'}$, and $R^{4'}$ is $R_dS(O)_2$—O—, or $(R_d)_2P(O)$—O— ($R_d$ is H, OH, alkyl, alkoxy, amino, or aryl, e.g., $R_d$ is ethyl).

Still another aspect of this invention relates to a compound of Formula (III):

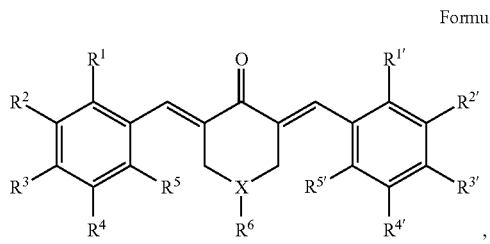

Formula (III)

wherein each of X is N or CH; each of $R^1$, $R^2$, $R^3$, $R^4$, $R^5$, $R^{1'}$, $R^{2'}$, $R^{3'}$, $R^{4'}$, and $R^{5'}$, independently, is H, alkyl (e.g., alkyl substituted with halo or $SO_2R_d$), halo, OH, $R_c$—O—, $R_dS(O)_2$—O—, or $(R_d)_2P(O)$—O—, $R_c$ being unsubstituted alkyl or alkyl substituted with halo, OH, alkoxy, amino, cycloalkyl, heterocycloalkyl, aryl, or heteroaryl, and $R_d$ being H, OH, alkyl, alkoxy, amino, or aryl; and $R^6$ is C(O)—$R_e$, C(O)$NR_eR_f$, or alkyl (e.g., unsubstituted alkyl or alkyl substituted with cycloalkyl), each of $R_e$ and $R_f$, independently, being alkyl or cycloalkyl.

Referring to Formula (III), a subset of compounds have one or more of the following features: X is N; $R^2$ is OH or R—O— (R is alkyl substituted with amino, e.g., R is $CH_2H_2N(C_2H_5)_2$); and $R^6$ is cyclopropylcarbonyl or cyclopropylmethyl.

The term "alkyl" refers to a saturated, linear or branched hydrocarbon moiety containing 1-10 carbon atoms, such as —$CH_3$ or —$CH(CH_3)_2$. The term "cycloalkyl" refers to a 3-10 membered, saturated, cyclic hydrocarbon moiety, such as cyclohexyl. The term "heterocycloalkyl" refers to a 3-10 membered, saturated, cyclic moiety having at least one ring heteroatom (e.g., N, O, or S), such as 4-tetrahydropyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Cycloalkyl, heterocycloalkyl, aryl, and heteroaryl can also be fused with each other.

The compounds described above include the compounds themselves, as well as their salts, prodrugs, and solvates, if applicable. A salt, for example, can be formed between an anion and a positively charged group (e.g., ammonium ion) on a 1,5-diphenyl-penta-1,4-dien-3-one compound. Suitable anions include chloride, bromide, iodide, sulfate, nitrate, phosphate, citrate, methanesulfonate, trifluoroacetate, acetate, succinate, malate, tosylate, tartrate, fumurate, glutamate, glucuronate, lactate, glutarate, and maleate. Likewise, a salt can also be formed between a cation and a negatively charged group (e.g., carboxylate) on a 1,5-diphenyl-penta-1,4-dien-3-one compound. Suitable cations include sodium ion, potassium ion, magnesium ion, calcium ion, and an ammonium cation. The compounds may also be in prodrug and solvate form. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

The compounds contain non-aromatic double bonds. Thus, they can occur as cis- or trans-isomeric forms. Such isomeric forms are contemplated.

Still another aspect of this invention relates to a method for treating cancer, inflammatory disease, or autoimmune disease. The method includes administering to a subject in need thereof an effective amount of one or more of the above described compounds.

Also within the scope of this invention is a composition containing one or more of the compounds described above and a pharmaceutically acceptable carrier for use in treating cancer/inflammatory disease/autoimmune disease, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

The compounds described above can be prepared by methods well known in the art. Schemes 1, 2, and 3 below demonstrate general synthetic routes used to synthesize compounds of formulas (I), (II), and (III), respectively.

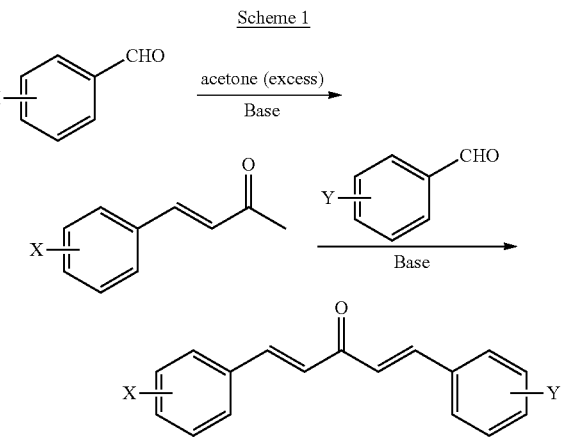

Scheme 1

As shown in Scheme 1 above, benzaldehyde is condensed with excessive acetone under a basic condition to give a 4-phenylbut-3-en-2-one compound, which is condensed with a second benzaldehyde compound to afford compounds of Formula (I). The thus-obtained product can be further modified to prepare other compounds of Formula (I).

As shown in Scheme 3 above, piperidin-4-one is reacted with acyl chloride or bromoalkane to give N-substituted piperidin-4-one, which is subsequently condensed with 2

Scheme 2

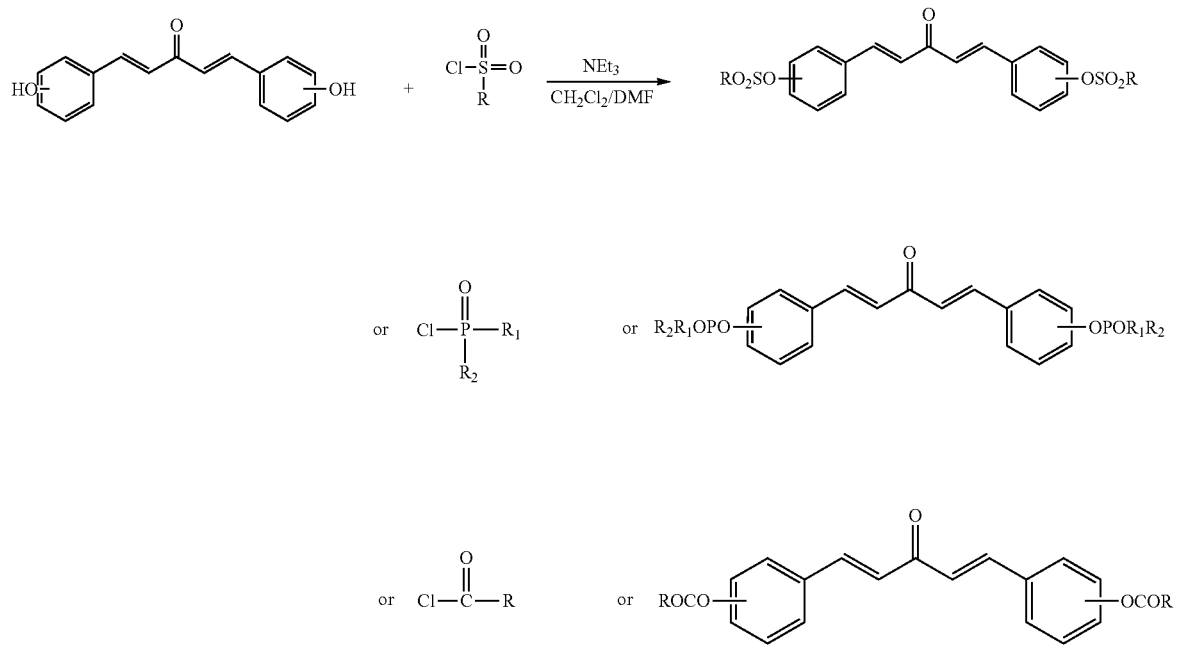

As shown in Scheme 2 above, hydroxyl-substituted 1,5-diphenylpenta-1,4-dien-3-one compounds (which can be prepared by the method described above) are condensed with sulfonyl chloride or chlorophosphine/phosphorochloridate/phosphoryl trichloride or acyl chloride to give compounds of Formula (II). Similarly, 3,5-dibenzylidenepiperidin-4-one compounds can be condensed with sulphonyl chloride/chlorophosphine/acyl chloride to give compounds also covered by Formula (II).

equivalents of benzaldehyde to afford symmetric 3,5-dibenzylidenepiperidin-4-one compounds covered by Formula (III). The N-substituted piperidin-4-one can be first reacted with 1 equivalent of benzaldehyde, and then with 1 equivalent of second benzaldehyde to prepare asymmetric 3,5-dibenzylidenepiperidin-4-one compounds, which are also covered by Formula (III).

Shown below are exemplary compounds of Formula (I), (II), and (III) prepared by the above-described methods:

Scheme 3

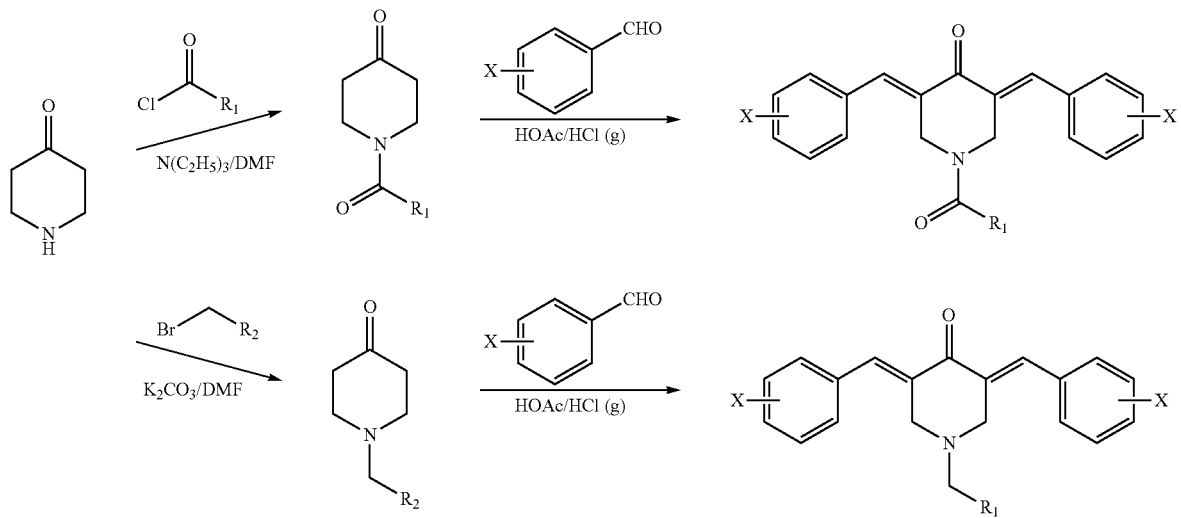

| Compound Nos. | Structures |
|---|---|
| 1 | 1-phenyl-5-(3-hydroxyphenyl)-1,4-pentadien-3-one |
| 2 | 1-(2-hydroxyphenyl)-5-(3-hydroxyphenyl)-1,4-pentadien-3-one |
| 3 | 1-(3,4-dihydroxyphenyl)-5-(3-hydroxyphenyl)-1,4-pentadien-3-one |
| 4 | 1-(3,4-dihydroxyphenyl)-5-(4-hydroxyphenyl)-1,4-pentadien-3-one |
| 5 | 1,5-bis(4-ethylsulfonyloxyphenyl)-1,4-pentadien-3-one |
| 6 | 1,5-bis(3-ethylsulfonyloxyphenyl)-1,4-pentadien-3-one |
| 7 | 1-phenyl-5-(3-ethylsulfonyloxyphenyl)-1,4-pentadien-3-one |
| 8 | 1,5-bis(3-methylsulfonyloxyphenyl)-1,4-pentadien-3-one |
| 9 | 1,5-bis(3-propylsulfonyloxyphenyl)-1,4-pentadien-3-one |
| 10 | 1,5-bis(3-phenylsulfonyloxyphenyl)-1,4-pentadien-3-one |

-continued
| Compound Nos. | Structures |
|---|---|
| 11 | 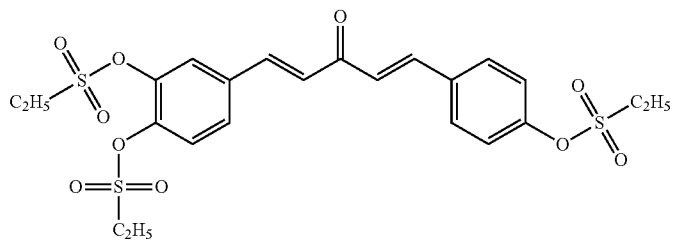 [SMILES: CCS(=O)(=O)Oc1ccc(/C=C/C(=O)/C=C/c2ccc(OS(=O)(=O)CC)c(OS(=O)(=O)CC)c2)cc1] |
| 12 | 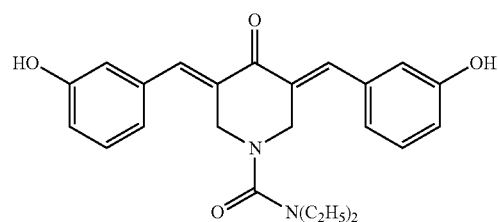 |
| 13 | 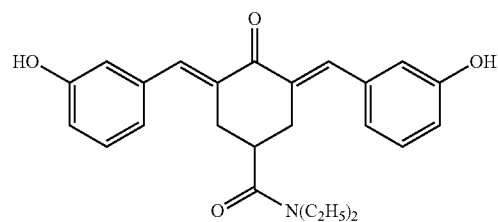 |
| 14 | 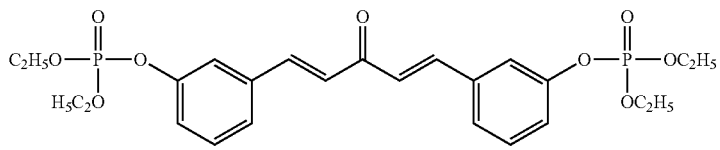 |
| 15 | 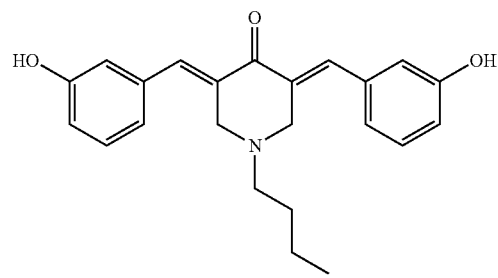 [SMILES: CCCCN1C/C(=C\c2cccc(O)c2)C(=O)/C(=C/c2cccc(O)c2)C1] |
| 16 | 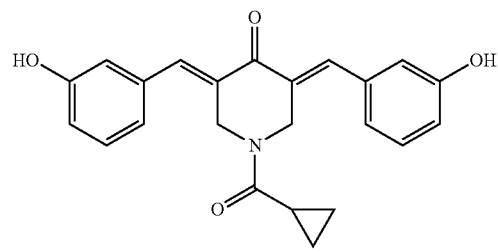 [SMILES: O=C1/C(=C/c2cccc(O)c2)CN(C(=O)C2CC2)C/C1=C\c1cccc(O)c1] |

-continued
| Compound Nos. | Structures |
|---|---|
| 17 | 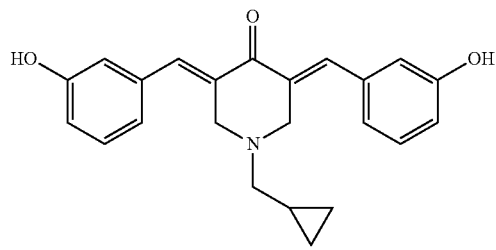 [SMILES: O=C1/C(=C/c2cccc(O)c2)CN(CC2CC2)C/C1=C\c1cccc(O)c1] |
| 18 | 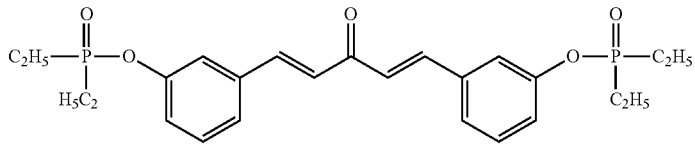 |
| 19 | 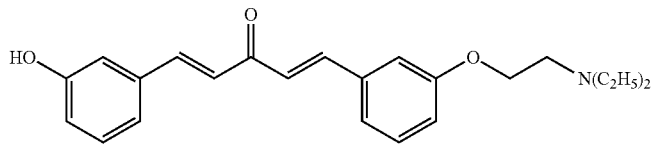 |
| 20 | 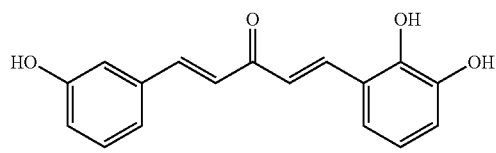 [SMILES: O=C(/C=C/c1cccc(O)c1)/C=C/c1cccc(O)c1O] |
| 21 | 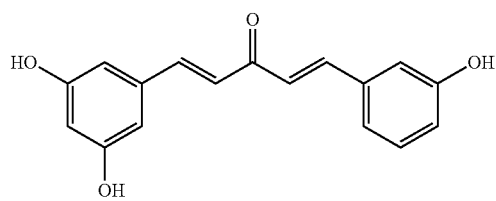 [SMILES: O=C(/C=C/c1cccc(O)c1)/C=C/c1cc(O)cc(O)c1] |
| 22 | 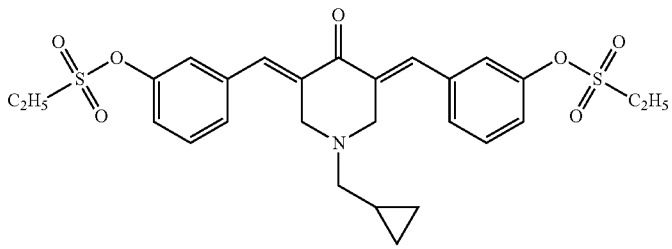 [SMILES: CCS(=O)(=O)Oc1cccc(/C=C2\CN(CC3CC3)C/C(=C\c3cccc(OS(=O)(=O)CC)c3)C2=O)c1] |
| 23 | 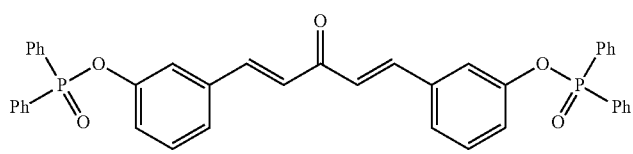 [SMILES: O=C(/C=C/c1cccc(OP(=O)(c2ccccc2)c2ccccc2)c1)/C=C/c1cccc(OP(=O)(c2ccccc2)c2ccccc2)c1] |
| 24 | 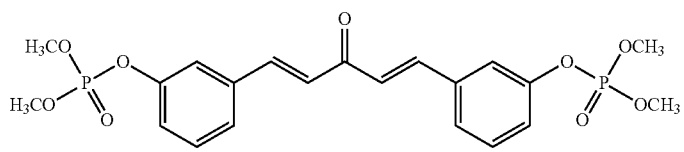 [SMILES: COP(=O)(OC)Oc1cccc(/C=C/C(=O)/C=C/c2cccc(OP(=O)(OC)OC)c2)c1] |

-continued
| Compound Nos. | Structures |
|---|---|
| 25 | 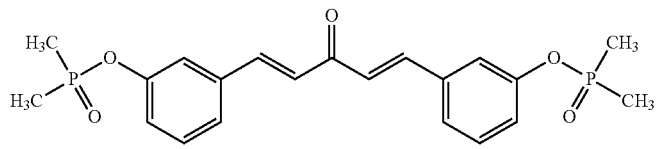 |
| 26 | 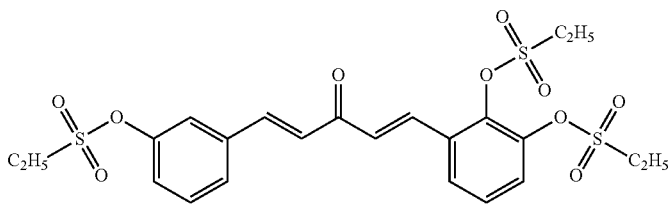 [SMILES: CCS(=O)(=O)Oc1cccc(/C=C/C(=O)/C=C/c2cccc(OS(=O)(=O)CC)c2OS(=O)(=O)CC)c1] |
| 27 | 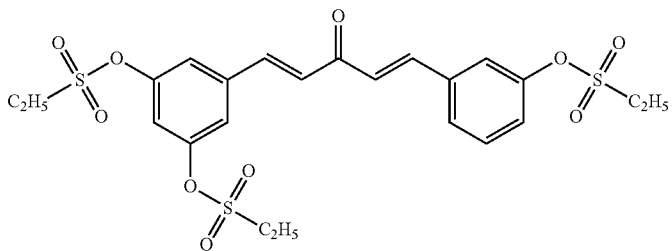 [SMILES: CCS(=O)(=O)Oc1cccc(/C=C/C(=O)/C=C/c2cc(OS(=O)(=O)CC)cc(OS(=O)(=O)CC)c2)c1] |
| 28 | 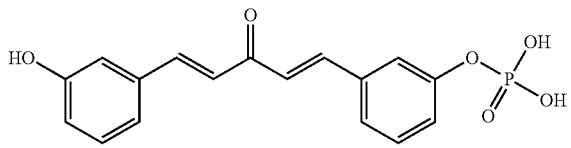 [SMILES: O=C(/C=C/c1cccc(O)c1)/C=C/c1cccc(OP(=O)(O)O)c1] |
| 29 | 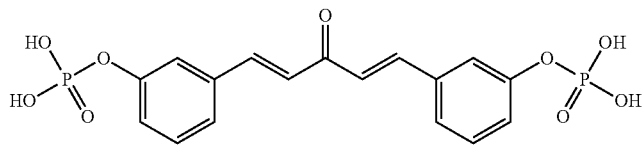 [SMILES: O=C(/C=C/c1cccc(OP(=O)(O)O)c1)/C=C/c1cccc(OP(=O)(O)O)c1] |
| 30 | 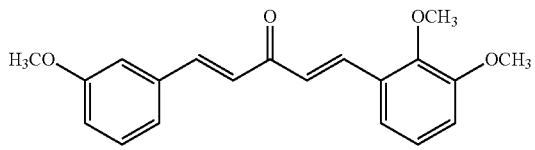 [SMILES: COc1cccc(/C=C/C(=O)/C=C/c2cccc(OC)c2OC)c1] |
| 31 | 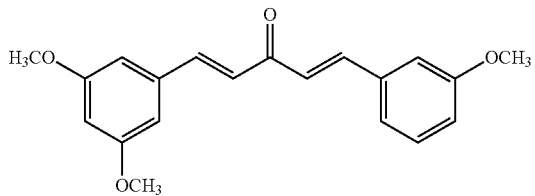 [SMILES: COc1cccc(/C=C/C(=O)/C=C/c2cc(OC)cc(OC)c2)c1] |
| 32 | 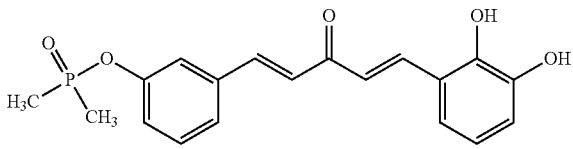 [SMILES: CP(C)(=O)Oc1cccc(/C=C/C(=O)/C=C/c2cccc(O)c2O)c1] |

-continued
| Compound Nos. | Structures |
|---|---|
| 33 | 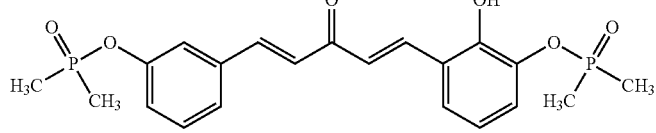 |
| 34 | 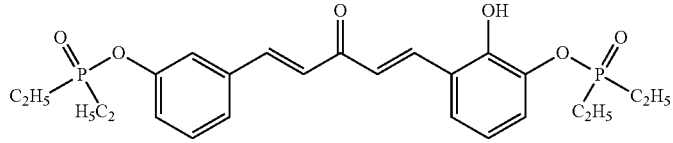 |
| 35 | 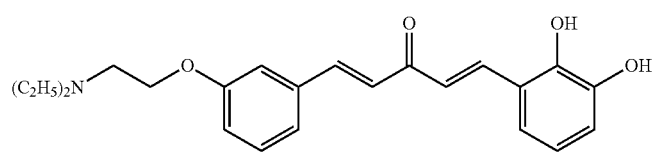 |
| 36 | 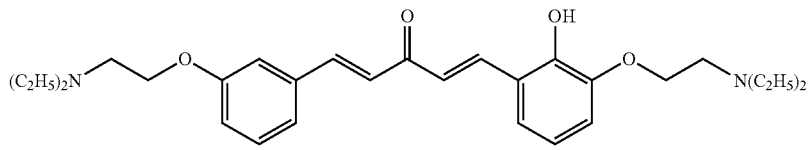 |
| 37 | 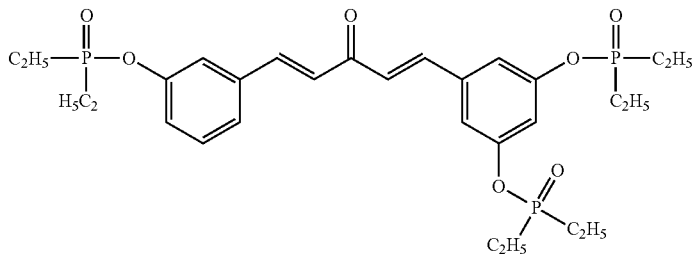 |
| 38 | 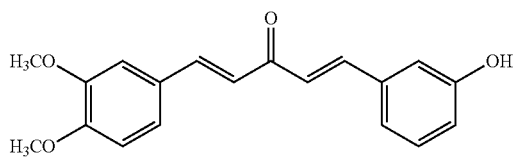 [SMILES: COc1ccc(/C=C/C(=O)/C=C/c2cccc(O)c2)cc1OC] |
| 39 | 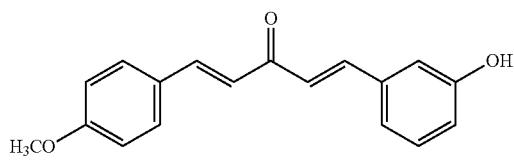 [SMILES: COc1ccc(/C=C/C(=O)/C=C/c2cccc(O)c2)cc1] |
| 40 | 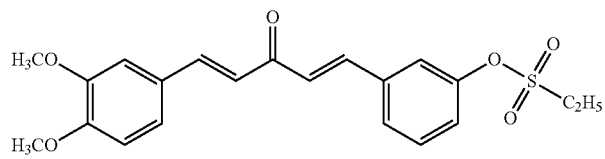 [SMILES: CCS(=O)(=O)Oc1cccc(/C=C/C(=O)/C=C/c2ccc(OC)c(OC)c2)c1] |
| 41 | 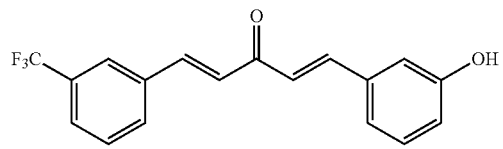 [SMILES: O=C(/C=C/c1cccc(O)c1)/C=C/c1cccc(C(F)(F)F)c1] |

| Compound Nos. | Structures |
|---|---|
| 42 | 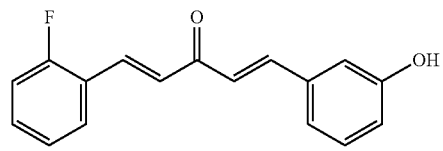 [SMILES: O=C(/C=C/c1cccc(O)c1)/C=C/c1ccccc1F] |
| 43 | 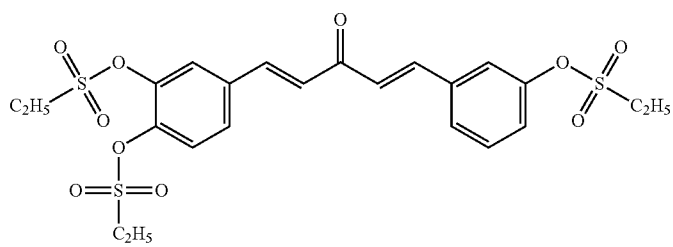 [SMILES: CCS(=O)(=O)Oc1cccc(/C=C/C(=O)/C=C/c2ccc(OS(=O)(=O)CC)c(OS(=O)(=O)CC)c2)c1] |
| 44 | 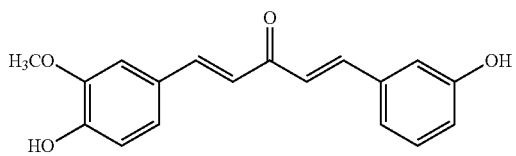 [SMILES: COc1cc(/C=C/C(=O)/C=C/c2cccc(O)c2)ccc1O] |
| 45 | 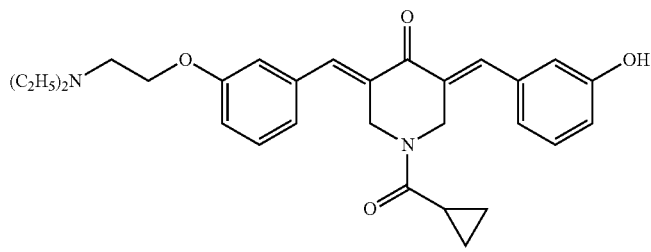 |
| 46 | 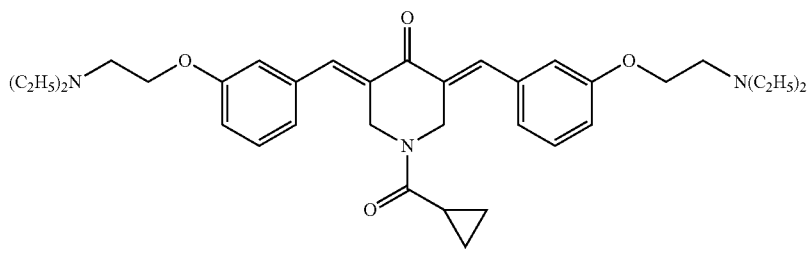 |
| 47 | 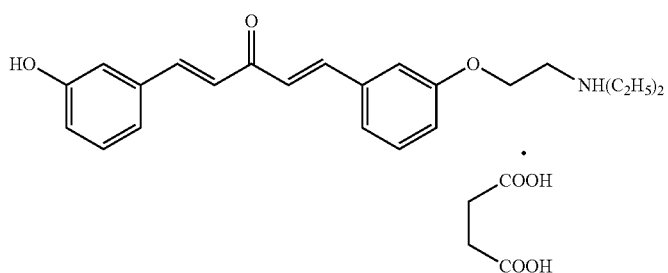 |
| 48 | 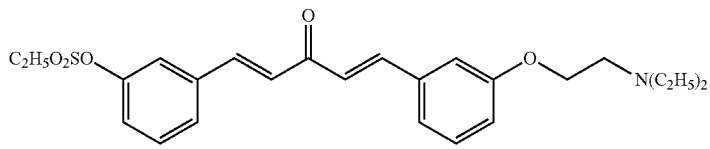 |

-continued
| Compound Nos. | Structures |
|---|---|
| 49 | 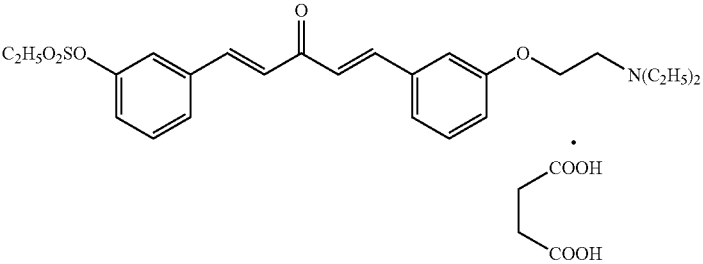 |
| 50 | 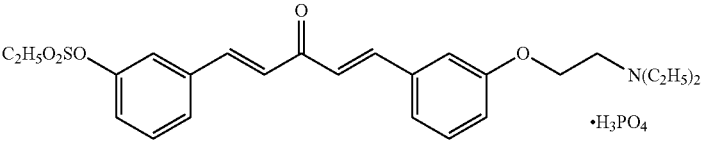 |
| 51 | 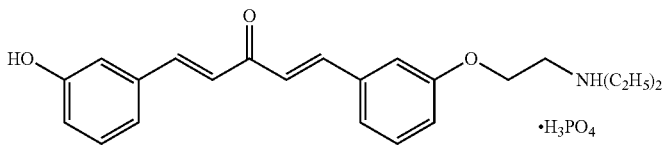 |
| 52 | 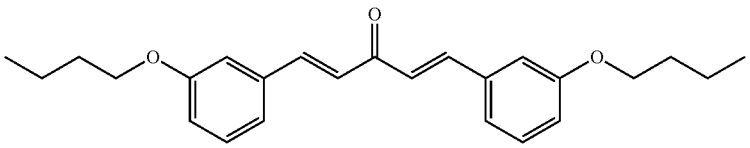 [SMILES: CCCCOc1cccc(/C=C/C(=O)/C=C/c2cccc(OCCCC)c2)c1] |
| 53 | 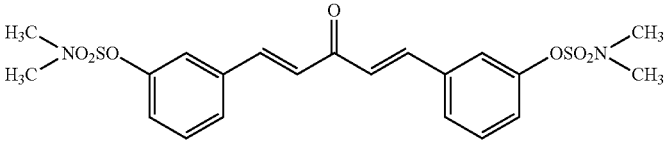 |
| 54 | 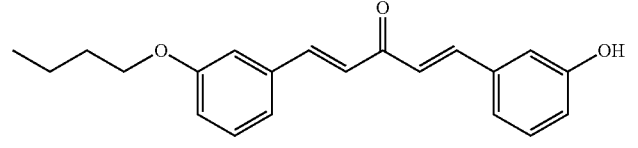 [SMILES: CCCCOc1cccc(/C=C/C(=O)/C=C/c2cccc(O)c2)c1] |
| 55 | 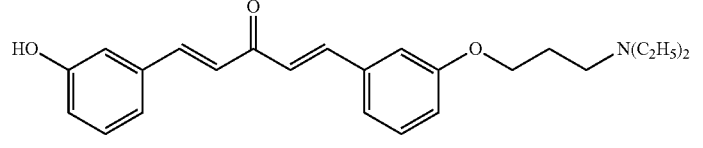 |
| 56 | 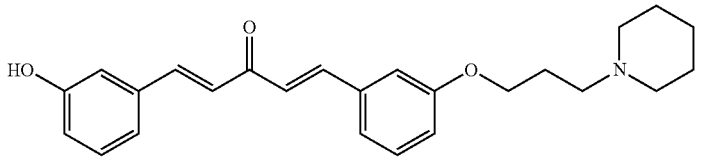 [SMILES: O=C(/C=C/c1cccc(O)c1)/C=C/c1cccc(OCCCN2CCCCC2)c1] |
| 57 | 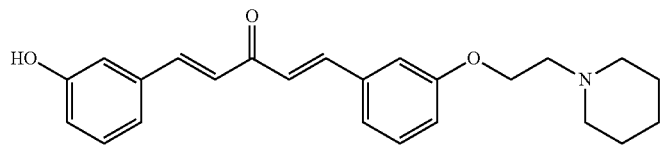 [SMILES: O=C(/C=C/c1cccc(O)c1)/C=C/c1cccc(OCCN2CCCCC2)c1] |

-continued

| Compound Nos. | Structures |
|---|---|
| 58 | 1-(3-hydroxyphenyl)-5-[3-(2-chloroethoxy)phenyl]-1,4-pentadien-3-one |
| 59 | 1-(3-hydroxyphenyl)-5-{3-[2-(morpholin-4-yl)ethoxy]phenyl}-1,4-pentadien-3-one |
| 60 | 1,5-bis[3-(ethylsulfonylmethyl)phenyl]-1,4-pentadien-3-one |
| 61 | 1,5-bis[3-(bromomethyl)phenyl]-1,4-pentadien-3-one |
| 62 | 1-(4-hydroxy-3-methylphenyl)-5-(4-methoxy-3-methylphenyl)-1,4-pentadien-3-one |
| 63 | 1,5-bis(4-hydroxy-2-methylphenyl)-1,4-pentadien-3-one |
| 64 | 1-(4-hydroxy-2-methylphenyl)-5-(4-methoxy-2-methylphenyl)-1,4-pentadien-3-one |
| 65 | 1,5-bis[4-(ethylsulfonyloxy)-3-methylphenyl]-1,4-pentadien-3-one |
| 66 | 1-(4-methoxy-3-methylphenyl)-5-[4-(ethylsulfonyloxy)-3-methylphenyl]-1,4-pentadien-3-one |

-continued

| Compound Nos. | Structures |
|---|---|
| 67 | 3-methyl-4-hydroxyphenyl / 3-methyl-4-(2-diethylaminoethoxy)phenyl dienone |
| 68 | 3-methyl-4-methoxyphenyl / 3-methyl-4-(2-diethylaminoethoxy)phenyl dienone |
| 69 | 2-methyl-4-(ethylsulfonyloxy)phenyl / 2-methyl-4-(ethylsulfonyloxy)phenyl dienone |
| 70 | 2-methyl-4-methoxyphenyl / 2-methyl-4-(ethylsulfonyloxy)phenyl dienone |
| 71 | 2-methyl-4-methoxyphenyl / 2-methyl-4-(2-diethylaminoethoxy)phenyl dienone |
| 72 | 2-methyl-4-hydroxyphenyl / 2-methyl-4-(2-diethylaminoethoxy)phenyl dienone |
| 73 | 3-hydroxyphenyl / 3-fluorophenyl dienone |
| 74 | 3-(ethylsulfonyloxy)phenyl / 3-fluorophenyl dienone |
| 75 | 3-hydroxyphenyl / 3-(trifluoromethoxy)phenyl dienone |

| Compound Nos. | Structures |
|---|---|
| 76 | C₂H₅O₂SO-[phenyl]-CH=CH-C(=O)-CH=CH-[phenyl]-O-CH₂CH₂-N(piperidine) |
| 77 | C₂H₅O₂SO-[phenyl]-CH=CH-C(=O)-CH=CH-[phenyl]-OCF₃ |
| 78 | H₃COCO-[phenyl]-CH=CH-C(=O)-CH=CH-[phenyl]-OCOCH₃ |
| 79 | C₂H₅O₂SO-[phenyl]-CH=CH-C(=O)-CH=CH-[phenyl]-O-CH₂CH₂-N(C₂H₅)₂ · HCl |

The compounds described above deactivate STAT proteins. Thus, this invention covers a method of administering an effective amount of one or more of the compounds to a patient having cancer, inflammatory disease, or autoimmune disease.

The term "treating" or "treatment" refers to administering one or more compounds to a subject, who has an above-described condition, a symptom of such a condition, or a predisposition toward such a condition, with the purpose to confer a therapeutic effect, e.g., to cure, relieve, alter, affect, ameliorate, or prevent the above-described disorder, the symptom of it, or the predisposition toward it. "An effective amount" refers to the amount of an active compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

Cancers that can be treated by the method of the invention include both solid and haematological tumors of various organs. Examples of solid tumors include pancreatic cancer, bladder cancer, colon cancer, colorectal cancer, breast cancer (e.g., metastatic breast cancer), prostate cancer (e.g., androgen-dependent, androgen-independent, or castrate-resistant prostate cancer), renal cancer (e.g., metastatic renal cell carcinoma), hepatocellular cancer, lung cancer (e.g., non-small cell lung cancer, bronchioloalveolar carcinoma, or adenocarcinoma of the lung), ovarian cancer (e.g., progressive epithelial or primary peritoneal cancer), cervical cancer, gastric cancer, esophageal cancer, head and neck cancer (e.g., squamous cell carcinoma of the head and neck), melanoma, neuroendocrine cancer (e.g., metastatic neuroendocrine tumors), brain tumors (e.g., glioma, anaplastic oligodendroglioma, adult glioblastoma multiforme, or adult anaplastic astrocytoma), bone cancer, and soft tissue sarcoma. Examples of haematological tumors include various leukemia (e.g., myeloid leukemia, chronic myelogenous leukemia or CML [accelerated CML and CML blast phase], acute lymphoblastic leukemia, or chronic lymphocytic leukemia), Hodgkin's disease, non-Hodgkin's lymphoma (e.g., follicular lymphoma or mantle cell lymphoma), B-cell lymphoma, T-cell lymphoma, multiple myeloma, Waldenstrom's macroglobulinemia, myelodysplastic syndromes (e.g., refractory anemia, refractory anemia with ringed sideroblasts, refractory anemia with excess blasts or RAEB, or RAEB in transformation), and myeloproliferative syndromes.

Inflammatory diseases that can be treated by the method of this invention include, but are not limited to, asthma, atherosclerosis, rheumatoid arthritis, inflammatory bowel diseases, Crohn, ulcerative colitis, ischemic heart disease, cardiomyopathy, glomerulonephritis, nephritic syndrome, hepatitis B or C infection, respiratory syncytial virus infection (pulmonary), and Guillain-Barré syndrome.

Autoimmune diseases that can be treated by the method of this invention include, but are not limited to, allergic encephalopathy, chronic obstructive pulmonary disease, psoriasis, psoriatic arthritis, diabetes mellitus, systemic lupus erythematosus, multiple sclerosis, polymyositis, dermatomyositis, mixed connective tissue disease, Sjögren's syndrome, Wegener's granulomatosis, polyarteritis nodosa, rheumatoid arthritis, and idiopathic thrombocytopenic purpura.

To practice the method of the present invention, a composition having one or more of the above-described compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active 1,5-diphenyl-penta-1,4-dien-3-one compound. Examples of other carriers include colloidal silicon oxide, magnesium stearate, cellulose, sodium lauryl sulfate, and D&C Yellow #10.

The 1,5-diphenyl-penta-1,4-dien-3-one compounds described above can be preliminarily screened for their efficacy in deactivating STAT proteins and treating above-described diseases by an in vitro assay and then confirmed by animal experiments and clinic trials. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Chemical Syntheses

Melting points were determined using a Fisher-John melting point apparatus without calibration. Proton Nuclear Magnetic Resonance ($^1$H NMR) and $^{13}$C NMR spectra were measured on Varian Gemini 300 or Inova 400 spectrometers with tetramethylsilane as the internal standard. Chemical shifts were reported in δ (ppm). Mass spectra (MS) were obtained on a Shimadzu LCMS-2010. A CombiFlash chromatographic system was performed over Grace silica gel cartridge for general separation and purification. Preparative thin layer chromatography using silica gel plates (Kieselgel 60, F254, 1.00 mm) were also used for separation and purification. Precoated silica gel plates (Kieselgel 60, F254, 0.25 mm) were used for thin layer chromatography (TLC) analysis. All reagents and solvents were purchased from Aldrich, Fisher, VWR, or other venders.

Synthesis of Compounds 1-4 and 21

Compounds 1-4 and 21 were prepared as shown in Scheme 4 below:

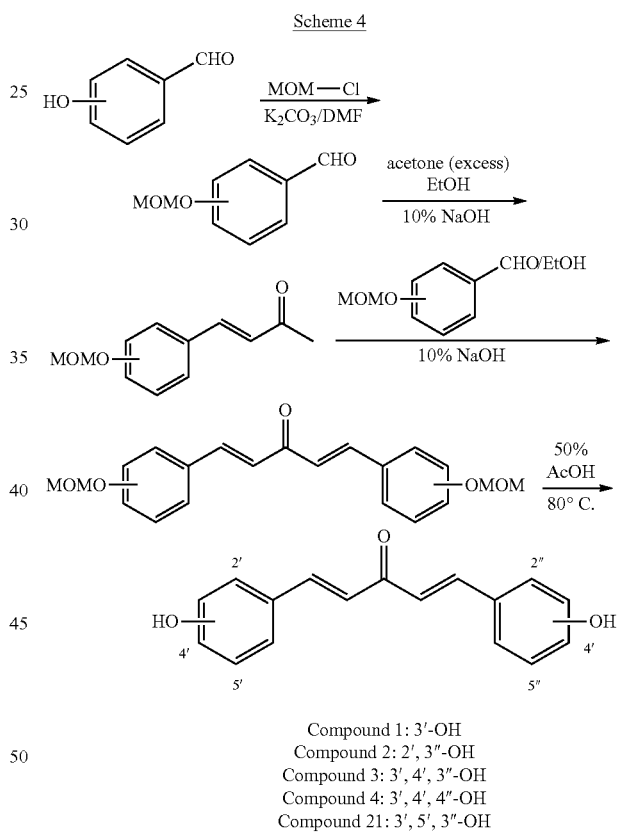

To a solution of hydroxyl benzaldehyde in DMF was added $K_2CO_3$ (2 eq. each hydroxyl group) at 4° C. in an ice-bath and methyl chloromethyl ether (MOM chloride) (1.3 eq. each hydroxyl group). After the solution was stirred at room temperature and monitored by TLC for 3-5 hours, hexanes/dichloromethane (1:1) was added and allowed to stir for 30 min. The solid was filtered out and the filtrate was concentrated. The resulting residue was diluted with EtOAc and washed with $H_2O$ twice. The aqueous layer was extracted with EtOAc. The combined organic layers were dried over $Na_2SO_4$ and concentrated. The crude was purified by a CombiFlash chromatography system using a Grace silica gel column and hexanes/ethyl acetate (as the eluent) to give MOM protected hydroxylbenzaldehyde. The resulting compound further reacted with excess acetone in ethanol catalyzed by 10% NaOH (1.2 eq. of NaOH). After stirred at room temperature and monitored by TLC for 1-5 hours, the reaction mixture was diluted with $CH_2Cl_2$, washed with $H_2O$ twice, and extracted with $CH_2Cl_2$ twice. The MOM protected hydroxyphenyl-but-3-en-2-one was obtained after purification by a CombiFlash system using hexanes/ethyl acetate as the eluent. The resulting compound reacted with an appropriate MOM protected hydroxybenaldehyde to afford MOM protected hydroxyl 1,5-diphenyl-penta-1,4-dien-3-one, which was deprotected by heating in 50% acetic acid aqueous solution to afford the desired product.

Compound 1: yellow crystalline solid; ESI MS m/z: 251.10 [M+H]$^+$; $^1$H NMR (300 MHz, CDCl$_3$) δ: 7.75 (d, 1H, J=15.0 Hz, H-1), 7.63 (d, 1H, J=15.0 Hz, H-5), 7.64 (m, 2H, aromatic ring H), 7.43-7.41 (m, 2H, aromatic ring H), 7.72-7.27 (m, 2H, aromatic ring H), 7.21-7.19 (d, 1H, J=6.0 Hz, aromatic ring H), 7.13-7.12 (m, 1H, aromatic ring H), 7.08 (d, 1H, J=15.0 Hz, H-2), 7.06 (d, 1H, J=15.0 Hz, H-4), 6.92-6.83 (m, 1H, aromatic ring H), 5.38 (br. 1H, OH).

Compound 2: yellow crystalline solid; ESI MS m/z: 267.29 [M+H]$^+$; $^1$H NMR (300 MHz, CD$_3$OD$_3$) δ: 8.10 (d, 1H, J=15.0 Hz, H-1), 7.63 (d, 1H, J=15.0 Hz, H-5), 7.75-7.62 (m, 1H, aromatic ring H), 7.25 (d, 1H, J=15.0 Hz, H-4), 7.22 (d, 1H, J=15.0 Hz, H-2), 7.21-7.11 (m, 4H, aromatic ring H), 6.91-6.84 (m, 3H, aromatic ring H), 3.68 (br. 2H, OH).

Compound 3: yellow crystalline solid; ESI MS m/z: 281.05 [M−H]$^-$; $^1$H NMR (300 MHz, CD$_3$OD$_3$) δ: 7.68 (d, 1H, J=15.9 Hz, H-5), 7.66 (d, 1H, J=15.9 Hz, H-1), 7.27-6.97 (m, 5H, aromatic ring H), 6.99 (d, 1H, J=15.9 Hz, H-4), 6.88-6.84 (m, 2H, aromatic ring H), 6.80 (d, 1H, J=15.9 Hz, H-2), 4.91 (br. 3H, OH).

Compound 4: yellow crystalline solid; ESI MS m/z: 281.05 [M−H]$^-$; $^1$H NMR (300 MHz, CD$_3$OD$_3$) δ: 7.70 (d, 1H, J=15.9 Hz, H-5), 7.65 (d, 1H, J=15.9 Hz, H-1), 7.60-7.56 (dd, 2H, aromatic ring H), 7.15-7.06 (m, 2H, aromatic ring H), 7.12 (d, 1H, J=15.9 Hz, H-4), 6.98 (d, 1H, J=15.9 Hz, H-2), 6.81 (t, 3H, J=8.4 Hz, aromatic ring H).

Compound 21: yellow crystalline solid; ESI MS m/z: 281.09 [M−H]$^-$; $^1$H NMR (300 MHz, CD$_3$OD$_3$) δ: 7.63 (d, 1H, J=15.9 Hz, H-5), 7.56 (d, 1H, J=15.9 Hz, H-1), 7.21-7.05 (m, 3H, aromatic ring H), 7.12 (d, 1H, J=15.9 Hz, H-4), 7.03 (d, 1H, J=15.9 Hz, H-2), 6.82-6.778 (m, 1H, aromatic ring H), 6.57 (d, 2H, J=2.1 Hz, aromatic ring H), 6.29 (t, 1H, J=2.1 Hz, aromatic ring H).

Syntheses of Compounds 20, 30, 31, 38, 39, 41, 42, 44, 62-64, 73, and 75

Compound 20, 30, 31, 38, 39, 41, 42, 44, 62-64, 73, and 75 were prepared as shown in Scheme 5 below:

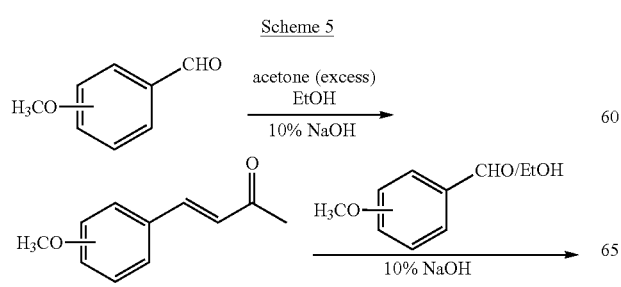

Scheme 5

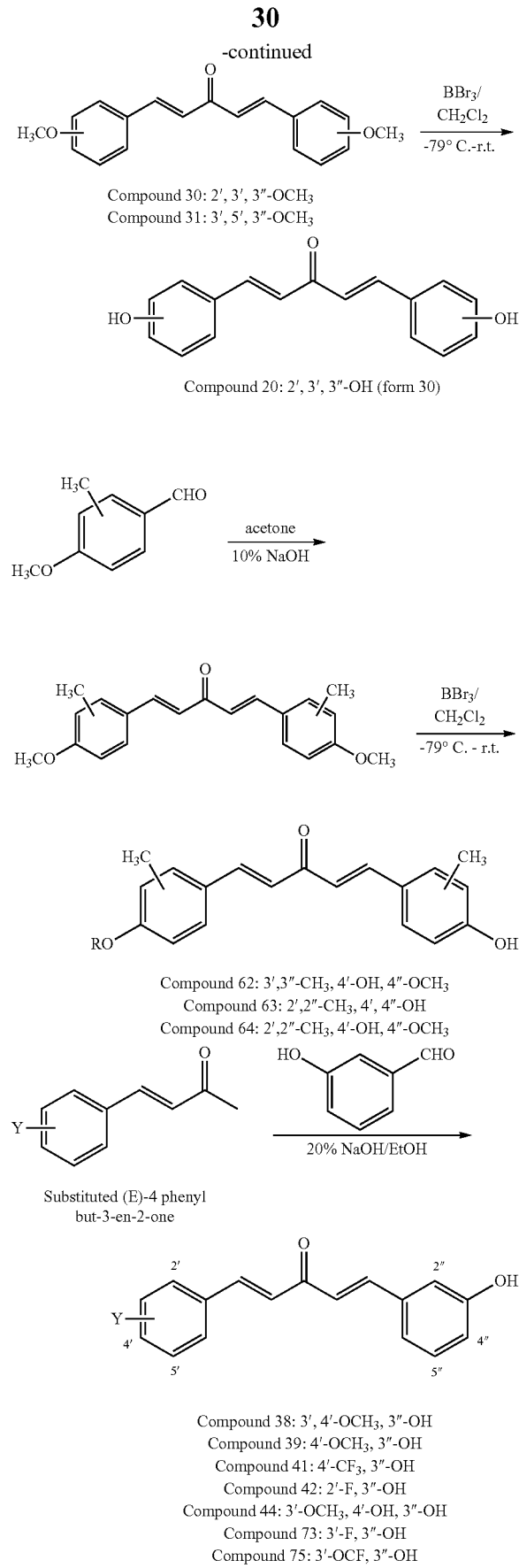

Compound 30: 2′, 3′, 3″-OCH$_3$
Compound 31: 3′, 5′, 3″-OCH$_3$

Compound 20: 2′, 3′, 3″-OH (form 30)

Compound 62: 3′,3″-CH$_3$, 4′-OH, 4″-OCH$_3$
Compound 63: 2′,2″-CH$_3$, 4′, 4″-OH
Compound 64: 2′,2″-CH$_3$, 4′-OH, 4″-OCH$_3$ Substituted (E)-4 phenyl but-3-en-2-one Compound 38: 3′, 4′-OCH$_3$, 3″-OH
Compound 39: 4′-OCH$_3$, 3″-OH
Compound 41: 4′-CF$_3$, 3″-OH
Compound 42: 2′-F, 3″-OH
Compound 44: 3′-OCH$_3$, 4′-OH, 3″-OH
Compound 73: 3′-F, 3″-OH
Compound 75: 3′-OCF, 3″-OH Methoxy substituted benzaldehyde was reacted with acetone followed by condensation with second methoxy substituted benzaldehyde in the same manner as described above to afford methoxy substituted 1,5-diphenyl-penta-1,4-dien-3-ones compounds 30 and 31 or methyl methoxy substituted 1,5-diphenyl-penta-1,4-dien-3-ones. Demethylation (or partial demethylation) with $BBr_3$ (2 eq. each methoxy group) in $CH_2Cl_2$ from −78° C. to 0° C. to room temperature gave the desired phenolic crude products. The reaction was monitored by TLC. After completion, the reaction mixture was poured into acidic ice/water and then extracted by ethyl ether. The desired products (i.e., compounds 20, 62-64) were obtained after purification over a CombiFlash chromatography system.

Compound 20: red crystalline solid; ESI MS m/z: 281.10 [M−H]$^-$; $^1$H NMR (300 MHz, $CD_3OD_3$) δ: 8.06 (d, 1H, J=15.9 Hz, H-5), 7.63 (d, 1H, J=15.9 Hz, H-1), 7.26-7.05 (m, 5H, aromatic ring H and H-2,4), 6.86-6.62 (m, 4H, aromatic ring H).

Compound 62: Amorphous, ESI MS m/z: 309.0 [M+H]$^+$; $^1$H NMR (400 MHz, acetone-$d_6$) δ: 8.03-7.94 (m, 2H, H-1,5), 7.15-7.00 (m, 3H, aromatic ring H), 6.96-6.87 (m, 3H, aromatic ring H), 6.68 (d, J=16.0 Hz, 1H, H-2), 6.65 (d, J=16.0 Hz, 1H, H-4), 3.85 (s, 3H, $OCH_3$), 2.12 (s, 3H, $CH_3$), 2.10 (s, 3H, $CH_3$).

Compound 63: Bright yellow solid, ESI MS m/z: 295.1 [M+H]$^+$; $^1$H NMR (400 MHz, $CD_3OD$) δ: 8.01 (d, 2H, J=15.6 Hz, H-1,5), 7.66-7.64 (m, 2H, aromatic ring H), 6.98 (d, 2H, J=15.6 Hz, H-2,4), 6.66-6.64 (m, 4H, aromatic ring H),), 2.40 (s, 6H, $CH_3$).

Compound 64: Amorphous, ESI MS m/z: 309.1 [M+H]$^+$; $^1$H NMR (400 MHz, acetone-$d_6$) δ: 8.07-7.94 (m, 2H, H-1,5), 7.75-7.67 and 7.08-7.01 (m, 1H, aromatic ring H), 7.50-7.44 (m, 2H, aromatic ring H), 6.83-6.73 (m, 1H, aromatic ring H), 6.70-6.66 (m, 2H, aromatic ring H),), 6.48 (d, J=16.0 Hz, 1H, H-2), 6.47 (d, J=16.0 Hz, 1H, H-4), 3.81 (s, 3H, $OCH_3$), 1.98 (s, 3H, $CH_3$), 1.94 (s, 3H, $CH_3$).

Compounds 38, 39, 41, 42, 44, 73, and 75 were synthesized by reaction of substituted benzaldehyde with (E)-4-(3-hydroxyphenyl)but-3-en-2-one in ethanol/20% NaOH aqueous solution at room temperature as shown in Scheme 5 above. The reactions were monitored by TLC. After completion, the solutions were neutralized by acetic acid, extracted with ethyl acetate, and concentrated to afford the desired products. To furnish Compound 44, the THP protecting group, which was introduced to make 3-methoxy-4-(tetrahydro-pyran-2-yloxy)-benzaldehyde, was removed by treating with 0.1 eq. pyridinium p-toluenesulfonate in ethanol solution at room temperature.

Compound 38: pale yellow needles; mp 159-160° C.; $C_{19}H_{18}O_4$, ESI-MS: m/z 311.2 [M+H]$^+$; $^1$H NMR (300 MHz, DMSO-$d_6$): 7.75, 7.65 (1H each, both d, J=16.2 Hz, H-1,5), 7.42 (1H, d, J=2.1 Hz, H-2'), 7.34 (1H, dd, J=2.1, 8.4 Hz, H-6'), 7.25, 7.23 (1H each, both d, J=16.2 Hz, H-2,4), 7.28-7.13 (2H, m, H-4", 5"), 7.14 (1H, br, t, H-2"), 7.04 (1H, d, J=8.4 Hz, H-5'), 6.86 (1H, br. d, 8.4 Hz, H-6"), 3.84, 3.82 (both s, 3H each, $OCH_3$×2).

Compound 39: yellow fine crystals; mp 152-153° C.; $C_{18}H_{16}O_3$, ESI-MS: m/z 281.2 [M+H]$^+$; $^1$H NMR (300 MHz, DMSO-$d_6$): 7.76, 7.62 (1H each, both d, J=16.2 Hz, H-1,5), 7.72 (2H, d, J=9.0 Hz, H-2', 6'), 7.22 (1H, d, 8.0 Hz, H-6"), 7.18, 7.17 (1H each, both d, J=16.2 Hz, H-2,4), 7.17 (1H, m, 5"), 7.09 (1H, br. 3, H-2"), 6.98 (2H, d, J=9.0 Hz, H-3', 5'), 6.81 (1H, br. d, 8.0 Hz, H-4"), 3.77 (s, 3H, $OCH_3$).

Compound 41: pale yellow needles; mp 138-139° C.; $C_{18}H_{13}F_3O_2$, ESI-MS: m/z 319.2 [M+H]$^+$; $^1$H NMR (300 MHz, DMSO-$d_6$): 8.14 (1H, br., H-2'), 8.07 (1H, br. d, J=7.8 Hz, H-6'), 7.81, 7.50 (1H each, both d, J=15.9 Hz, H-1, 2), 7.78-7.62 (2H, m, H-4', 5'), 7.69, 7.19 (1H each, both d, J=16.2 Hz, H-4, 5), 7.22 (2H, 4", 5"), 7.10 (1H, br. s, H-2"), 6.83 (1H, br. d, J=8.7 Hz, H-6").

Compound 42: pale yellow fine crystals; mp 159-160° C.; $C_{17}H_{13}FO_2$, ESI-MS: m/z 269.2 [M+H]$^+$; $^1$H NMR (300 MHz, DMSO-$d_6$): 7.92 (1H, dt, J=1.8, 7 Hz, H-4'), 7.73, 7.42 (1H each, both d, J=16.2 Hz, H-1, 2), 7.69, 7.16 (1H each, both d, J=16.2, Hz, H-4, 5), 7.47 (1H, m, H-5-"), 7.30-7.12 (3H, m, 2', 5', 6', 4"), 7.10 (1H, br. s, H-2"), 6.82 (1H, dt, J=1.8, 7.2 Hz, H-6").

Compound 44: yellow fine crystals; mp 144-145° C.; $C_{23}H_{26}O_{10}S_3$, ESI-MS: m/z 559.1 [M+H]$^+$; $^1$H NMR (300 MHz, DMSO-$d_6$): 7.63-6.93 (11H, m, aromatic H and vinyl H), 3.81 (2H, s, $OCH_3$).

Compound 73: Off-white solid, ESI MS m/z: 269.5 [M+H]$^+$; $^1$H NMR (400 MHz, $CDCl_3$) δ: 7.68 (d, J=16.0 Hz, 1H, H-1), 7.67 (d, J=16.0 Hz, 1H, H-5), 7.37-7.35 (m, 2H, aromatic ring H), 7.29-7.24 (m, 2H, aromatic ring H), 7.18-7.16 (m, 1H, aromatic ring H), 7.11-7.08 (m, 2H, aromatic ring H)), 7.04 (d, J=16.0 Hz, 1H, H-4), 7.01 (d, J=16.0 Hz, 1H, H-2), 6.91-6.88 (m, 1H, aromatic ring H).

Compound 75: Light yellow solid, ESI MS m/z: 335.5 [M+H]$^+$; $^1$H NMR (400 MHz, $CDCl_3$) δ: 7.69 (d, J=15.6 Hz, 1H, H-1), 7.67 (d, J=15.6 Hz, 1H, H-5), 7.49-7.47 (m, 1H, aromatic ring H), 7.42-7.39 (m, 2H, aromatic ring H), 7.28-7.22 (m, 2H, aromatic ring H), 7.16-7.14 (m, 2H, aromatic ring H),), 7.05 (d, J=16.0 Hz, 1H, H-4), 7.02 (d, J=16.0 Hz, 1H, H-2), 6.95-6.92 (m, 1H, aromatic ring H).

Syntheses of Compounds 12, 13, and 15-17

Compounds 12, 13, and 15-17 were synthesized as shown in Scheme 6, by methods modified based on that described in Roberta Costi, et al., Bioorganic & Medicinal Chemistry 2004, 12: 199-215.

Scheme 6

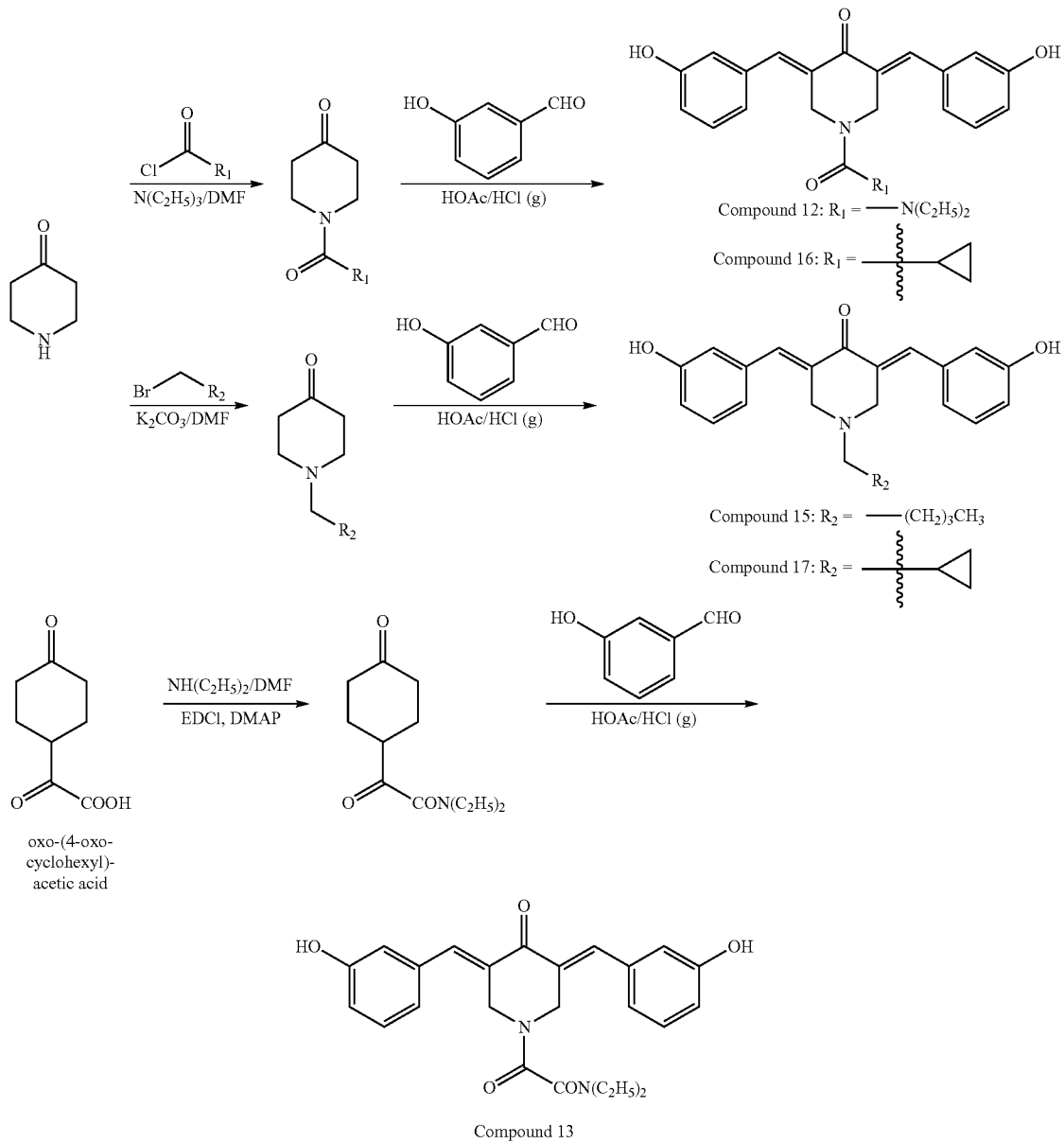

To a solution of piperidin-4-one in DMF was added triethylamine (1.5 eq.) and N,N-diethylacetamide chloride (1.5 eq.). The resulting solution was stirred at room temperature for 5 hours or until completion observed by TLC. The solvent was evaporated and the residue was partitioned in H₂O and EtOAc. The aqueous layer was extracted with EtOAc and the combined organic layers were dried over Na₂SO₄ and concentrated. The crude product was purified by a CombiFlash chromatography system using silica gel cartridge and CH₂Cl₂/MeOH gradient eluent to afford 4-oxo-piperidine-1-carboxylic acid diethylamide, which was subsequently reacted with 3-hydroxybenzaldehyde (2.5 eq.) in acetic acid (99.7%) and purged with HCl gas (0.5-1 h). After stirring at room temperature for 3 hours, the solvent was evaporated and the crude was purified by a Combiflash chromatography system with hexanes/EtOAc as eluent, followed by crystallization from MeOH, to afford Compound 12 as a yellow crystalline solid.

Compound 12: yellow crystalline solid; ESI MS m/z: 407.49 [M+H]⁺; ¹H NMR (300 MHz, CD₃OD) δ: 7.61 (s. 2H, benzylidene C$\underline{H}$=), 7.16 (t, 2H, J=7.5 Hz, aromatic ring H), 6.82-6.79 (m, 2H, aromatic ring H), 6.75-6.71 (m, 4H, aromatic ring H), 4.36 (s, 4H, 4-oxo-piperidine-H-2, 6), 2.95 (q, 4H, —NC$\underline{H}$₂CH₃), 0.71 (t, 6H, —NCH₂C$\underline{H}$₃).

Compound 16 was prepared in the same manner as described above except that cyclopropanecarbonyl chloride (1.5 eq.) was used instead of N,N-diethylacetamide chloride.

Compound 16: yellow solid; ESI MS m/z: 376.16 [M+H]⁺; ¹H NMR (300 MHz, DMSO-d₆) δ: 7.59 (s. 2H, benzylidene C$\underline{H}$=), 7.30 (t, 2H, J=7.5 Hz, aromatic ring H), 6.98-6.93 (m, 4H, aromatic ring H), 6.87-6.85 (m, 2H, aromatic ring H), 3.39 (s, 4H, 4-oxo-piperidine-H-2, 6), 1.69 (m, 1H, cyclopropanecarbonyl C$\underline{H}$), 0.62-0.58 (m, 4H, cyclopropanecarbonyl C$\underline{H}_2$).

Compounds 15 and 17 were synthesized by reaction of piperidin-4-one with 1-bromo-butane (1.5 eq.) or bromo methyl-cyclopropane (1.5 eq.) in DMF in the presence of $K_2CO_3$. After stirring at room temperature for 24 h or monitored by MS, the reaction solvent was removed by evaporation. The residue was partitioned in $H_2O$ and EtOAc, and the organic layer was washed with $H_2O$ twice. The aqueous then was extracted with EtOAc and the extract was dried over $Na_2SO_4$. The crude product was purified by a Combiflash chromatography system using silica gel cartridge and $CH_2Cl_2$/MeOH gradient eluent. The obtained N-substituted 4-oxo-piperidine compound was condensed with 3-hydroxybenzaldehyde (2.5 eq.), following the same procedure described above, to afford the desired product.

Compound 15: yellow solid; ESI MS m/z: 364.19 [M+H]$^+$; $^1$H NMR (300 MHz, CD$_3$OD) δ: 7.64 (s. 2H, benzylidene C$\underline{H}$=), 7.21 (t, 2H, J=8.1 Hz, aromatic ring H), 6.85 (d, br, 2H, J=8.1 Hz, aromatic ring H), 6.80-6.76 (m, 4H, aromatic ring H), 3.80 (s, 4H, 4-oxo-piperidine-H-2, 6), 2.50 (t, 2H, J=8.1 Hz, —NC$\underline{H}_2$CH$_2$—), 1.42-1.30 (m, 2H, —NCH$_2$C$\underline{H}_2$CH$_2$—), 1.27-1.14 (m, 2H, —NCH$_2$CH$_2$C$\underline{H}_2$CH$_3$), 0.81 (t, 3H, —NCH$_2$CH$_2$CH$_2$C$\underline{H}_3$).

Compound 17: yellow solid; ESI MS m/z: 362.18 [M+H]$^+$; $^1$H NMR (300 MHz, DMSO-d$_3$) δ: 7.66 (s. 2H, benzylidene C$\underline{H}$=), 7.21 (t, 2H, J=7.8 Hz, aromatic ring H), 6.86 (d, br, 2H, J=7.2 Hz, aromatic ring H), 6.81-6.75 (m, 4H, aromatic ring H), 3.90 (s, 4H, 4-oxo-piperidine-H-2, 6), 2.40 (d, 2H, J=6.6 Hz, methylene-cyclopropane-C$\underline{H}_2$), 0.65 (m, 1H, cyclopropane C$\underline{H}$), 0.43-0.37 (m, 2H, cyclopropane C$\underline{H}_2$), 0.11-0.07 (m, 2H, cyclopropane C$\underline{H}_2$).

Compound 13 was synthesized starting from treating oxo-(4-oxo-cyclohexyl)-acetic acid with 1-ethyl-3-(3-dimethylaminopropyl)carbodiimide (2 eq.) and 4-dimethylaminopyridine (catalytic amount) in DMF. After stirring at room temperature for approximately 10 min., the reaction mixture was cooled in an ice-bath and diethylamine (1.5 eq.) was added. The resulting mixture was stirred at room temperature for 5 hours with TLC monitoring. The solvent was removed by evaporation. The residue was diluted with EtOAc and washed with $H_2O$ twice. The aqueous then was extracted with EtOAc and the organic layer was dried over $Na_2SO_4$. The desired intermediate N,N-diethyl-2-oxo-2-(4-oxo-cyclohexyl)-acetamide was obtained after purification through a combiflash chromatography system using a silica gel cartridge and $CH_2Cl_2$/MeOH gradient eluent, which further condensed with 3-hydroxybenzaldehyde (2.5 eq.) by following the same procedure described above to get the desired product as a yellow solid ESI MS m/z: 406.51 [M+H]$^+$; $^1$H NMR (300 MHz, DMSO-d$_6$) δ: 7.54 (s. 2H, benzylidene C$\underline{H}$=), 7.25 (t, 2H, J=7.8 Hz, aromatic ring H), 6.93-6.89 (m, 4H, aromatic ring H), 6.81-6.78 (m, 2H, aromatic ring H), 3.23 (q, 4H, J=7.2 Hz, —NC$\underline{H}_2$CH$_3$), 2.95 (m, 4H, 4-oxo-cyclohexyl-H-2,6), 2.54 (m, 1H, cyclohexyl-H-1), 0.94 (m, 6H, —NCH$_2$C$\underline{H}_3$).

Syntheses of Compounds 5-11, 14, 18, 22-29, 32-34, 37, 40, 43, 53, 65-66, 69-70, 74, 77, and 78

Syntheses of these compounds are shown in Scheme 7.

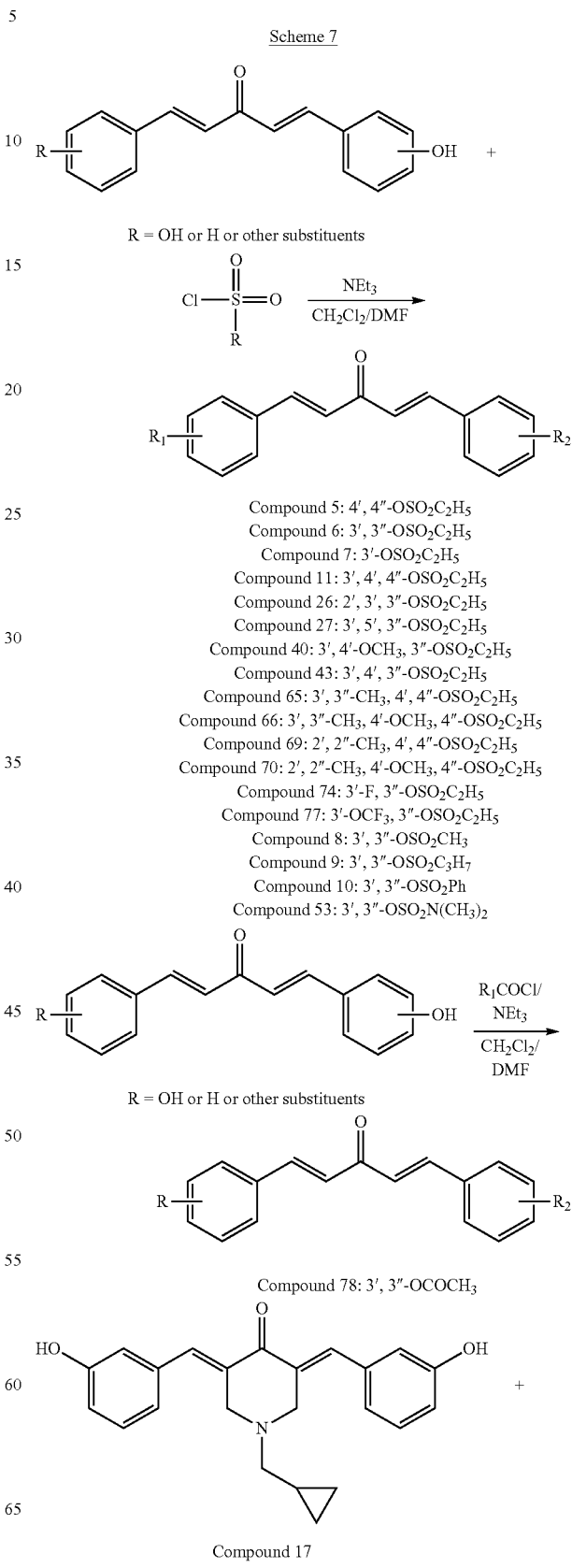

Scheme 7

R = OH or H or other substituents

Compound 5: 4′, 4″-OSO$_2$C$_2$H$_5$
Compound 6: 3′, 3″-OSO$_2$C$_2$H$_5$
Compound 7: 3′-OSO$_2$C$_2$H$_5$
Compound 11: 3′, 4′, 4″-OSO$_2$C$_2$H$_5$
Compound 26: 2′, 3′, 3″-OSO$_2$C$_2$H$_5$
Compound 27: 3′, 5′, 3″-OSO$_2$C$_2$H$_5$
Compound 40: 3′, 4′-OCH$_3$, 3″-OSO$_2$C$_2$H$_5$
Compound 43: 3′, 4′, 3″-OSO$_2$C$_2$H$_5$
Compound 65: 3′, 3″-CH$_3$, 4′, 4″-OSO$_2$C$_2$H$_5$
Compound 66: 3′, 3″-CH$_3$, 4′-OCH$_3$, 4″-OSO$_2$C$_2$H$_5$
Compound 69: 2′, 2″-CH$_3$, 4′, 4″-OSO$_2$C$_2$H$_5$
Compound 70: 2′, 2″-CH$_3$, 4′-OCH$_3$, 4″-OSO$_2$C$_2$H$_5$
Compound 74: 3′-F, 3″-OSO$_2$C$_2$H$_5$
Compound 77: 3′-OCF$_3$, 3″-OSO$_2$C$_2$H$_5$
Compound 8: 3′, 3″-OSO$_2$CH$_3$
Compound 9: 3′, 3″-OSO$_2$C$_3$H$_7$
Compound 10: 3′, 3″-OSO$_2$Ph
Compound 53: 3′, 3″-OSO$_2$N(CH$_3$)$_2$ R = OH or H or other substituents Compound 78: 3′, 3″-OCOCH$_3$ Compound 17

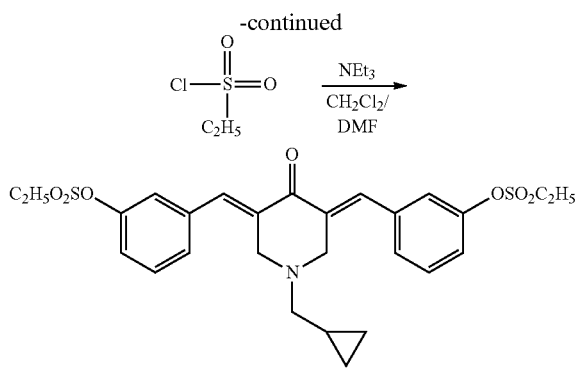

Compound 22

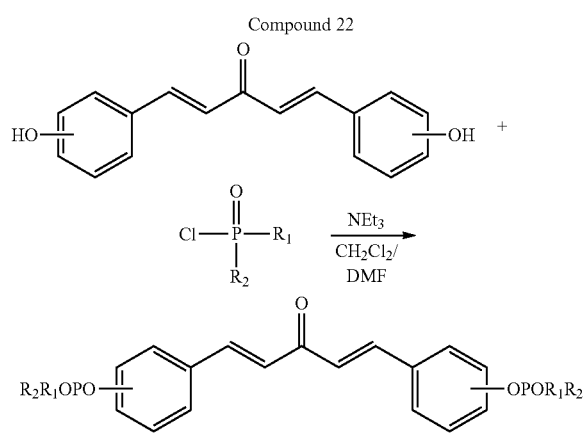

Compound 14: 3', 3"-OPO(OC₂H₅)₂
Compound 18: 3', 3"-OPO(C₂H₅)₂
Compound 23: 3', 3"-OPO(Ph)₂
Compound 24: 3', 3"-OPO(OCH₃)₂
Compound 25: 3', 3"-OPO(CH₃)₂
Compound 32: 2', 3'-OH, 3"-OPO(CH₃)₂
Compound 33: 3', 3"-OPO(CH₃)₂, 2'-OH
Compound 34: 3', 3"-OPO(C₂H₅)₂, 2'-OH
Compound 37: 3', 5', 3"-OPO(C₂H₅)₂,

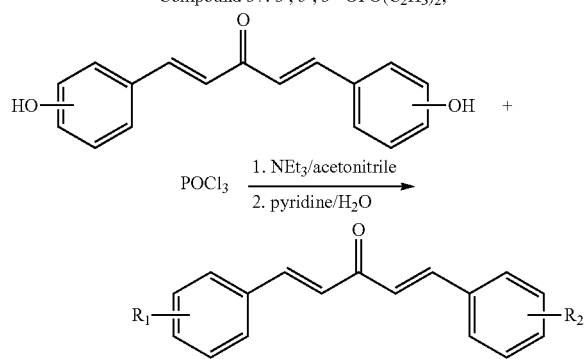

Compound 28: 3'-OH, 3"-OPO(OH)₂
Compound 29: 3', 3"-OPO(OH)₂

To a solution of 1,5-bis-(3-hydroxy-phenyl)-penta-1,4-dien-3-one (synthesized by the method shown in Scheme 4) in CH₂Cl₂ (containing a small amount of DMF) was slowly added ethanesulfonyl chloride (~10 eq.) and Et₃N (~10 eq.). The resulting mixture was stirred at room temperature for 4-5 hours. The reaction mixture was diluted with CH₂Cl₂, washed with water twice, and extracted with CH₂Cl₂. The organic extract was dried over Na₂SO₄, filtered, and concentrated to get crude as a yellow solid. The crude was purified by quick column filtration, then crystallization, and re-crystallization from EtOAc to get the desired product compound 6 as a light yellow crystalline solid. Yield>78%. ESI MS m/z: 451.2 [M+H]⁺; ¹H NMR (300 MHz, CDCl₃) δ: 7.71 (d, 2H, J=15.9 Hz, H-1,5), 7.57-7.53 (m, 4H, aromatic ring H), 7.47 (t, 2H, J=7.8 Hz, aromatic ring H), 7.34-7.31 (m, 2H, aromatic ring H), 7.08 (d, 2H, J=15.9 Hz, H-2,4), 3.34 (q, 4H, J=7.5 Hz, —OSO₂CH₂CH₃), 1.58 (t, 6H, J=7.5 Hz, —OSO₂CH₂CH₃).

Compounds 5, 7-11, 22, 26, 27, 40, 43, 53, 65-66, 69-70, 74, and 77 were synthesized in the manner similar to that described above.

Compound 5: a light yellow crystalline solid; ESI MS m/z: 451.2 [M+H]⁺; ¹H NMR (300 MHz, CDCl₃) δ: 7.72 (d, 2H, J=15.9 Hz, H-1,5), 7.66 (d, 4H, J=8.7 Hz, aromatic ring H), 7.34 (d, 4H, J=8.7 Hz, aromatic ring H), 7.04 (d, 2H, J=15.9 Hz, H-2,4), 3.33 (q, 4H, J=7.5 Hz, —OSO₂CH₂CH₃), 1.57 (t, 6H, J=7.5 Hz, —OSO₂CH₂CH₃).

Compound 7: yellow crystalline solid; ESI MS m/z: 343.4 [M+H]⁺; ¹H NMR (300 MHz, CDCl₃) δ: 7.76 (d, 1H, J=15.9 Hz, H-5), 7.70 (d, 1H, J=15.9 Hz, H-1), 7.65-7.62 (m, 2H, aromatic ring H), 7.57-7.53 (m, 2H, aromatic ring H), 7.49-7.42 (m, 4H, aromatic ring H), 7.34-7.30 (m, 1H, aromatic ring H), 7.10 (d, 1H, J=15.9 Hz, H-4), 7.09 (d, 1H, J=15.9 Hz, H-2), 3.33 (q, 2H, J=7.5 Hz, —OSO₂CH₂CH₃), 1.58 (t, 3H, J=7.5 Hz, —OSO₂CH₂CH₃).

Compound 8: off-white crystalline solid; ESI MS m/z: 423.2 [M+H]⁺; ¹H NMR (300 MHz, CDCl₃) δ: 7.70 (d, 2H, J=15.9 Hz, H-1,5), 7.58-7.38 (m, 4H, aromatic ring H), 7.48 (t, 2H, J=7.5 Hz, aromatic ring H), 7.36-7.33 (m, 2H, aromatic ring H), 7.08 (d, 2H, J=15.9 Hz, H-2,4), 3.21 (s, 6H, —OSO₂CH₃).

Compound 9: yellow crystalline solid; ESI MS m/z: 479.2 [M+H]⁺; ¹H NMR (300 MHz, CDCl₃) δ: 7.71 (d, 2H, J=15.9 Hz, H-1,5), 7.57-7.53 (m, 4H, aromatic ring H), 7.47 (t, 2H, J=7.8 Hz, aromatic ring H), 7.34-7.31 (m, 2H, aromatic ring H), 7.08 (d, 2H, J=15.9 Hz, H-2,4), 3.31-3.26 (m, 4H, —OSO₂CH₂CH₂CH₃), 2.12-1.99 (m, 4H, —OSO₂CH₂CH₂CH₃), 1.16 (t, 6H, J=7.5 Hz, —OSO₂CH₂CH₂CH₃).

Compound 10: light yellow thick oil; ESI MS m/z: 547.2 [M+H]⁺; ¹H NMR (300 MHz, CDCl₃) δ: 7.88-7.85 (m, 4H, phenyl sulfonate aromatic ring H), 7.71 (t, 2H, phenyl sulfonate aromatic ring H), 7.59 (d, 2H, J=15.9 Hz, H-1,5), 7.59-7.48 (m, 6H, phenyl sulfonate substituted and biphenyl aromatic ring H), 7.35 (t, 2H, J=7.8 Hz, aromatic ring H), 7.27-7.25 (m, 2H, biphenyl aromatic ring H), 7.03-7.00 (m, 2H, biphenyl aromatic ring H), 6.95 (d, 2H, J=15.9 Hz, H-2, 4).

Compound 11: a light yellow crystalline solid; ESI MS m/z: 559.1 [M+H]⁺; ¹H NMR (300 MHz, CDCl₃) δ: 7.73 (d, 1H, J=15.9 Hz, H-5), 7.72-7.70 (dd, 1H, aromatic ring H), 7.67 (d, 1H, J=15.9 Hz, H-1), 7.67 (d, 2H, J=8.7 Hz, 2",6"aromatic ring H), 7.55-7.50 (m, 2H, aromatic ring H), 7.34 (d, 2H, J=8.7 Hz, 3",5"aromatic ring H), 7.05 (d, 1H, J=15.9 Hz, H-4), 7.03 (d, 1H, J=15.9 Hz, H-2), 3.47 (m, 6H, —OSO₂CH₂CH₃), 1.58 (m, 9H, —OSO₂CH₂CH₃).

Compound 26: amorphous; ESI MS m/z: 559.1 [M+H]⁺; ¹H NMR (300 MHz, CDCl₃) δ: 8.02 (d, 1H, J=15.9 Hz, H-1), 7.72-7.70 (dd, 1H, aromatic ring H), 7.73 (d, 1H, J=15.9 Hz, H-5), 7.59-7.33 (m, 6H, aromatic ring H), 7.20 (d, 1H, J=15.9 Hz, H-2), 7.07 (d, 1H, J=15.9 Hz, H-4), 3.58 (q, 2H, J=7.5 Hz, —OSO₂CH₂CH₃), 3.45 (q, 2H, J=7.5 Hz, —OSO₂CH₂CH₃), 3.35 (q, 2H, J=7.5 Hz, —OSO₂CH₂CH₃), 1.67 (t, 3H, J=7.5 Hz, —OSO₂CH₂CH₃), 1.63-1.56 (m, 6H, —OSO₂CH₂CH₃).

Compound 27: amorphous; ESI MS m/z: 559.1 [M+H]⁺; ¹H NMR (300 MHz, CDCl₃) δ: 7.71 (d, 1H, J=15.9 Hz, H-1), 7.65 (d, 1H, J=15.9 Hz, H-5), 7.54-7.39 (m, 5H, aromatic ring H), 7.34-7.25 (m, 2H, aromatic ring H), 7.09 (d, 1H, J=15.9 Hz, H-2), 7.06 (d, 1H, J=15.9 Hz, H-4), 3.40-3.01 (m, 6H, —OSO$_2$C$\underline{H}_2$CH$_3$), 1.61-156 (m, 9H, —OSO$_2$CH$_2$C$\underline{H}_3$).

Compound 40: oily syrups; C$_{21}$H$_{22}$O$_6$S, ESI-MS: m/z 403.2 [M+H]$^+$; $^1$H NMR (300 MHz, DMSO-d$_6$): 7.77-6.99 (11H, m, aromatic H and vinyl H), 3.80 (3H each, s, OC$\underline{H}_3$), 3.77 (3H each, s, OC$\underline{H}_3$), 3.50 (2H, m, SO$_2$C$\underline{H}_2$CH$_3$), 1.34 (3H, m, SO$_2$CH$_2$C$\underline{H}_3$).

Compound 43: pale yellow needles, mp 102-103° C.; C$_{23}$H$_{26}$O$_{10}$S$_3$, ESI-MS: m/z 559.1 [M+H]$^+$; $^1$H NMR (300 MHz, DMSO-d$_6$): 7.89-7.35 (11H, m, aromatic H and vinyl H), 3.62 (4H, m, SO$_2$C$\underline{H}_2$CH$_3$×2), 3.53 (2H, q, J=7.5 Hz, SO$_2$C$\underline{H}_2$CH$_3$), 1.37 (9H, m, SO$_2$CH$_2$C$\underline{H}_3$×3).

Compound 22: yellow solid; ESI MS m/z: 546.19 [M+H]$^+$; $^1$H NMR (300 MHz, CDCl$_3$) δ: 7.77 (s, 2H, benzylidene C$\underline{H}$=), 7.50-7.28 (m, 8H, aromatic ring H), 3.92 (s, 4H, cyclohexyl-H-3,5), 3.35-3.25 (m, 6H, —OSO$_2$C$\underline{H}_2$CH$_3$), 2.46 (d, 2H, J=6.6 Hz, —C$\underline{H}_2$), 1.59-1.50 (m, 9H, —OSO$_2$CH$_2$C$\underline{H}_3$), 0.86 (m, 1H, cyclopropanyl C$\underline{H}$), 0.50-0.44 (m, 2H, cyclopropanyl C$\underline{H}_2$), 0.15-0.08 (m, 2H, cyclopropanecarbonyl C$\underline{H}_2$).

Compound 53: Yellow oily, ESI MS m/z: 481.0 [M+H]$^+$; $^1$H NMR (400 MHz, CD$_3$OD) δ: 7.68 (d, 2H, J=16.2 Hz, H-1,5), 7.63-7.54 (m, 2H, aromatic ring H), 7.46-7.39 (m, 1H, aromatic ring H), 7.33-7.01 (m, 4H, aromatic ring H; 2H, H-2,4 benzylidene C$\underline{H}$=), 6.84-6.81 (m, 1H, aromatic ring H), 2.95 (s, 12H, —OSO$_2$N(C$\underline{H}_3$)$_2$).

Compound 65: Amorphous, ESI MS m/z: 479.6 [M+H]$^+$; $^1$H NMR (400 MHz, CDCl$_3$) δ: 7.65 (d, 2H, J=16.0 Hz, H-1,5), 7.48 (br, 2H, aromatic ring H), 7.46-7.43 (m, 2H, aromatic ring H), 7.31 (d, 2H, J=8.4 Hz, aromatic ring H), 6.99 (d, 2H, J=16.0 Hz, H-2,4), 3.36 (q, 4H, J=7.2 Hz, —OSO$_2$C$\underline{H}_2$CH$_3$), 2.37 (s, 6H, CH$_3$), 1.57 (t, 6H, J=7.2 Hz, —OSO$_2$CH$_2$C$\underline{H}_3$).

Compound 66: Orange-yellowish solid, ESI MS m/z: 401.6 [M+H]$^+$; $^1$H NMR (400 MHz, CDCl$_3$) δ: 7.67 (d, 1H, J=16.0 Hz, H-1), 7.63 (d, 1H, J=16.0 Hz, H-5), 7.48-7.40 (m, 4H, aromatic ring H), 7.30 (d, 1H, J=8.4 Hz, aromatic ring H), 6.00 (d, 1H, J=16.0 Hz, H-2), 5.91 (d, 1H, J=16.0 Hz, H-4), 6.82 (d, 1H, J=8.4 Hz, aromatic ring H), 3.86 (s, 3H, OCH$_3$), 3.36 (q, 2H, J=7.2 Hz, —OSO$_2$C$\underline{H}_2$CH$_3$), 2.37 (s, 3H, CH$_3$), 2.23 (s, 3H, CH$_3$), 1.57 (t, 3H, J=7.2 Hz, —OSO$_2$CH$_2$C$\underline{H}_3$).

Compound 69: Brownish solid, ESI MS m/z: 479.6 [M+H]$^+$; $^1$H NMR (400 MHz, CDCl$_3$) δ: 7.94 (d, 2H, J=16.0 Hz, H-1,5), 7.65 (d, 2H, J=8.4 Hz, aromatic ring H), 7.14-7.12 (m, 4H, aromatic ring H), 6.92 (d, 2H, J=16.0 Hz, H-2,4), 3.28 (q, 4H, J=7.2 Hz, —OSO$_2$C$\underline{H}_2$CH$_3$), 2.46 (s, 6H, —C$\underline{H}_3$), 1.53 (t, 6H, J=7.2 Hz, —OSO$_2$CH$_2$C$\underline{H}_3$).

Compound 70: Light brownish solid, ESI MS m/z: 401.1 [M+H]$^+$; $^1$H NMR (400 MHz, CDCl$_3$) δ: 7.99 (d, 1H, J=15.6 Hz, H-1), 7.91 (d, 1H, J=15.6 Hz, H-5), 7.65-7.61 (m, 2H, aromatic ring H), 7.14-7.12 (m, 3H, aromatic ring H), 6.93 (d, 1H, J=15.6 Hz, H-2), 6.86 (d, 1H, J=15.6 Hz, H-4), 6.77-6.74 (m, 1H, aromatic ring H), 3.82 (s, 3H, OCH$_3$), 3.29 (q, 2H, J=7.2 Hz, —OSO$_2$C$\underline{H}_2$CH$_3$), 2.46 (s, 6H, CH$_3$), 1.53 (t, 3H, J=7.2 Hz, —OSO$_2$CH$_2$C$\underline{H}_3$).

Compound 74: Light yellowish solid, ESI MS m/z: 361.1 [M+H]$^+$; $^1$H NMR (400 MHz, CDCl$_3$) δ: 7.66 (d, 2H, J=16.0 Hz, H-1,5), 7.52-7.50 (m, 2H, aromatic ring H), 7.45-7.41 (m, 1H, aromatic ring H), 7.37-7.35 (m, 2H, aromatic ring H), 7.30-7.28 (m, 2H, aromatic ring H), 7.11-7.08 (m, 1H, aromatic ring H), 7.04 (d, 1H, J=16.0 Hz, H-2), 7.03 (d, 1H, J=16.0 Hz, H-4), 3.26 (q, 2H, J=7.6 Hz, —OSO$_2$C$\underline{H}_2$CH$_3$), 1.55 (t, 3H, J=7.6 Hz, —OSO$_2$CH$_2$C$\underline{H}_3$).

Compound 77: Yellowish solid, ESI MS m/z: 427.1 [M+H]$^+$; $^1$H NMR (400 MHz, CDCl$_3$) δ: 7.68 (d, 2H, J=16.0 Hz, H-1,5), 7.53-7.51 (m, 3H, aromatic ring H), 7.46-7.41 (m, 3H, aromatic ring H), 7.31-7.26 (m, 2H, aromatic ring H), 7.05 (dd, 2H, J=16.0, 1.6 Hz, H-2,4), 3.31 (q, 2H, J=7.2 Hz, —OSO$_2$C$\underline{H}_2$CH$_3$), 1.55 (t, 3H, J=7.2 Hz, —OSO$_2$CH$_2$C$\underline{H}_3$).

Compound 78 was synthesized in the manner similar to that in which 1,5-bis-(3-hydroxy-phenyl)-penta-1,4-dien-3-one was synthesized. Acetic chloride (3 eq.) was used instead of ethanesulfonyl chloride. After stirring at room temperature for 3-4 h, the reaction mixture was poured into water, and extracted with CH$_2$Cl$_2$. The combined organic layers were washed with water and then brine, dried over Na$_2$SO$_4$, filtered and concentrated to give a light yellow solid crude product. Purification with CombiFlash chromatograph using n-hexane/EtOAc as eluent gave the desired compound in quantitative yield. Light yellowish crystalline solid, ESI MS m/z: 351.1 [M+H]$^+$; $^1$H NMR (400 MHz, CDCl$_3$) δ: 7.67 (d, 2H, J=16.0 Hz, H-1,5), 7.46-7.38 (m, 4H, aromatic ring H), 7.34-7.33 (m, 2H, aromatic ring H), 7.14-7.11 (m, 2H, aromatic ring H), 7.02 (d, 2H, J=16.0, H-2,4), 2.31 (s, 6H, —COCH$_3$).

Compounds 14 and 24 were synthesized in the manner similar to that in which 1,5-bis-(3-hydroxy-phenyl)-penta-1,4-dien-3-one was synthesized. Phosphorochloridic acid diethyl ester (~10 eq. for Compound 14) or phosphorochloridic acid dimethyl ester (~10 eq. for Compound 24) were used instead of ethanesulfonyl chloride. After stirring at room temperature for 2 hour, the reaction mixture was poured into water, and extracted with CH$_2$Cl$_2$. The combined organic layers were washed with water and then brine, dried over Na$_2$SO$_4$, filtered and concentrated to give a yellow solid crude product. Purification with CombiFlash chromatograph using CH$_2$Cl$_2$/MeOH as eluent gave the desired compounds in quantitative yield.

Compound 14: amorphous; ESI MS m/z: 539.22 [M+H]$^+$; $^1$H NMR (300 MHz, CDCl$_3$) δ: 7.69 (d, 2H, J=15.9 Hz, H-1,5), 7.51 (br. 2H, aromatic ring H), 7.46-7.39 (m, 4H, aromatic ring H), 7.32-7.28 (m, 2H, aromatic ring H), 7.09 (d, 2H, J=15.9 Hz, H-2,4), 4.32-4.22 (m, 8H, OC$\underline{H}_2$CH$_3$), 1.41 (t, 12H, J=7.2 Hz, OCH$_2$C$\underline{H}_3$).

Compound 24: amorphous, ESI MS m/z: 483.09 [M+H]$^+$; $^1$H NMR (300 MHz, CDCl$_3$) δ: 7.69 (d, 2H, J=15.9 Hz, H-1,5), 7.49-7.37 (m, 6H, aromatic ring H), 7.28-7.25 (m, 2H, aromatic ring H), 7.06 (d, 2H, J=15.9 Hz, H-2,4), 3.91 (s, 6H, OC$\underline{H}_3$), 3.87 (s, 6H, OCH$_3$).

Compounds 18, 23, 25, 32-34, and 37 were synthesized in the manner similar to that described above. Diethyl chlorophosphine (~10-15 eq.) was used to prepare Compounds 18, 35, and 38, diphenyl chlorophosphine (~10 eq.) was used to make Compound 23, and dimethyl chlorophosphine (~10 eq.) was used to make Compounds 25, 32, and 33. After stirring at room temperature for 2 h; the reaction mixture was poured into water and extracted with CH$_2$Cl$_2$. The organic layer was washed with water and brine, dried over Na$_2$SO$_4$, filtered, and concentrated to give the crude compound as a yellow solid. Purification with CombiFlash chromatograph using CH$_2$Cl$_2$/MeOH as the eluent gave the desired compound in quantitative yield.

Compound 18: amorphous; ESI MS m/z: 475.22 [M+H]$^+$; $^1$H NMR (300 MHz, CDCl$_3$) δ: 7.70 (d, 2H, J=15.9 Hz, H-1,5), 7.52 (d, 2H, J=0.9 Hz, aromatic ring H), 7.40-7.27 (m, 6H, aromatic ring H), 7.09 (d, 2H, J=15.9 Hz, H-2,4), 1.99-1.86 (m, 8H, C$\underline{H}_2$CH$_3$), 1.30-1.16 (m, 12H, CH$_2$C$\underline{H}_3$).

Compound 23: yellow crystalline solid; ESI MS m/z: 667.61 [M+H]$^+$; $^1$H NMR (300 MHz, CDCl$_3$) δ: 7.95-7.88 (m, 8H, aromatic ring H), 7.76-7.67 (m, 2H, aromatic ring H), 7.60 (d, 2H, J=15.9 Hz, H-1,5), 7.55-7.26 (m, 18H, aromatic ring H), 6.97 (d, 2H, J=15.9 Hz, H-2,4).

Compound 25: yellow crystalline solid; ESI MS m/z: 419.07 [M+H]$^+$; $^1$H NMR (300 MHz, CDCl$_3$) δ: 7.70 (d, 2H, J=15.9 Hz, H-1,5), 7.50 (d, 2H, J=1.5 Hz, aromatic ring H), 7.45-7.37 (m, 4H, aromatic ring H), 7.30-7.26 (m, 2H, aromatic ring H), 7.08 (d, 2H, J=15.9 Hz, H-2,4), 1.71 (s, 6H, $CH_3$), 1.67 (s, 6H, $CH_3$).

Compound 32: light orange solid; ESI MS m/z: 381.14 [M+Na]$^+$; $^1$H NMR (400 MHz, $CD_3OD$) δ: 8.09 (d, 1H, J=16.0 Hz, H-1), 7.65 (d, 1H, J=16.0 Hz, H-5), 7.26 (d, 1H, J=16.0 Hz, H-2), 7.15 (d, 1H, J=16.0 Hz, H-4), 7.23 (t, 1H, J=8.0 Hz, aromatic ring H), 7.15-7.08 (m, 3H, aromatic ring H), 6.85-6.81 (m, 2H, aromatic ring H), 6.70 (t, 1H, J=8.0 Hz, aromatic ring H), 1.26 (s, 6H, $CH_3$).

Compound 33: yellow solid; ESI MS m/z: 457.14 [M+Na]$^+$; $^1$H NMR (400 MHz, $CD_3OD$) δ: 8.11 (d, 1H, J=16.0 Hz, H-1), 7.70 (d, 1H, J=16.0 Hz, H-5), 7.56-7.54 (m, 1H, aromatic ring H), 7.44 (t, 1H, J=8.0 Hz, aromatic ring H), 7.28 (d, 1H, J=16.0 Hz, H-2), 7.15 (d, 1H, J=16.0 Hz, H-4), 7.28-7.21 (m, 1H, aromatic ring H), 7.15-7.08 (m, 3H, aromatic ring H), 6.84-6.82 (m, 1H, aromatic ring H), 6.70 (t, 1H, J=8.0 Hz, aromatic ring H), 1.72 (s, 3H, $CH_3$), 1.68 (s, 3H, $CH_3$), 1.27-1.19 (m, 6H, $CH_3$).

Compound 34: amorphous; ESI MS m/z: 489.08 [M−H]$^−$; $^1$H NMR (400 MHz, $CDCl_3$) δ: 8.14 (d, 1H, J=15.2 Hz, H-1), 7.73 (d, 1H, J=15.2 Hz, H-5), 7.58-7.56 (m, 2H, aromatic ring H), 7.48-7.45 (m, 1H, aromatic ring H), 7.33-7.28 (m, 3H, aromatic ring H), 7.17-7.14 (m, 1H, aromatic ring H), 6.87-6.71 (m, 2H, H-2,4), 2.03-1.98 (m, 4H, $CH_2CH_3$), 1.86-1.66 (m, 4H, $CH_2CH_3$), 1.28-1.13 (m, 12H, $CH_2CH_3$).

Compound 37: amorphous; ESI MS m/z: 595.08 [M−H]$^−$; $^1$H NMR (400 MHz, $CDCl_3$) δ: 7.77 (d, 1H, J=15.6 Hz, H-5), 7.69 (d, 1H, J=15.6 Hz, H-1), 7.56-7.53 (m, 2H, aromatic ring H), 7.44-7.40 (m, 2H, aromatic ring H), 7.32-7.14 (m, 4H, aromatic ring H and H-2,4), 7.02-6.93 (m, 1H, aromatic ring H), 2.02-1.89 (m, 12H, $CH_2CH_3$), 1.26-1.06 (m, 18H, $CH_2CH_3$).

Compounds 28 and 29 were synthesized by the following procedure. A solution of 1,5-bis-(3-hydroxy-phenyl)-penta-1,4-dien-3-one (synthesized by the method illustrated in Scheme 4) (0.16 mmol) in acetonitrile was cooled to −78° C. To this was added $Et_3N$ (20 eq.) and fresh distilled $POCl_3$ (10 eq.) in acetonitriles. The resulting mixture was stirred at −78° C. for 2.5 hours or monitored by TLC. After completion, the reaction solution was warmed to 0° C. and water (~1 mL) and pyridine (0.4 mL) were added. The resulting reaction mixture was stirred at 0° C. to room temperature for 1.5 hours and concentrated to dryness. The crude as a mixture of Compounds 28 or 29 was purified by revered-phase column chromatograph using C18 silica gel and MeOH/$H_2O$ to afford the desired products.

Compound 28: yellow solid; ESI MS m/z: 377.01 [M−H+MeOH]$^+$; $^1$H NMR (300 MHz, $D_2O$) δ: 7.63 (d, 2H, J=15.9 Hz, H-1,5), 7.45-7.38 (m, 6H, aromatic H), 7.24-7.21 (m, 2H, aromatic H), 7.11 (d, 2H, J=15.9 Hz, H-2,4).

Compound 29: yellow solid; ESI MS m/z: 425.1 [M−H]$^+$; $^1$H NMR (300 MHz, $D_2O$) δ: 7.47 (d, 2H, J=15.9 Hz, H-1,5), 7.40-7.26 (m, 6H, aromatic H), 7.21 (br, 2H, aromatic H), 6.95 (d, 2H, J=15.9 Hz, H-2,4).

Syntheses of Compounds 19, 35-36, 45-46, 48, 52, 54-59, and 76

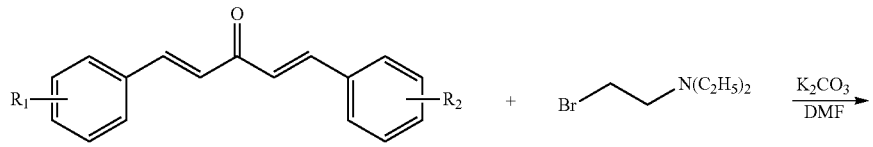

1,5-bis-(3-hydroxy-phenyl)-penta-1,4-dien-3-one: 3′, 3″-OH,
Compound 20: 2′, 3′, 3″-OH,
Compound 62: 3′, 3″-$CH_3$, 4′-OH, 4″-$OCH_3$
Compound 62a: 3′, 3″-$CH_3$, 4′, 4″-OH,
Compound 63: 2′, 2″-$CH_3$, 4′, 4″-OH,
Compound 64: 2′, 2″-$CH_3$, 4′-OH, 4″-$OCH_3$

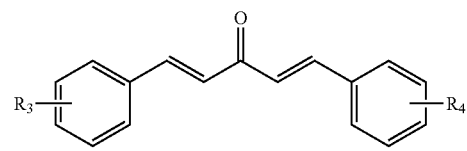

Compound 19: 3′-OH, 3″-O($CH_2$)$_2$N($C_2H_5$)$_2$
Compound 35: 2′, 3′-OH, 3″-O($CH_2$)$_2$N($C_2H_5$)$_2$
Compound 36: 2′-OH, 3′, 3″-O($CH_2$)$_2$N($C_2H_5$)$_2$
Compound 67: 3′, 3″,-$CH_3$, 4′-O($CH_2$)$_2$N($C_2H_5$)$_2$, 4″-OH
Compound 68: 3′, 3″-$CH_3$, 4′-O($CH_2$)$_2$N($C_2H_5$)$_2$, 4″-$OCH_3$
Compound 71: 2′, 2″-$CH_3$, 4′-O($CH_2$)$_2$N($C_2H_5$)$_2$, 4″-$OCH_3$
Compound 72: 2′, 2″-$CH_3$, 4′-O($CH_2$)$_2$N($C_2H_5$)$_2$, 4″-OH

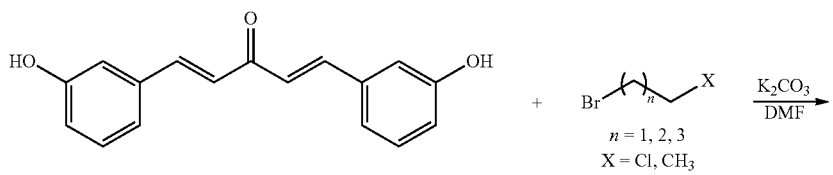

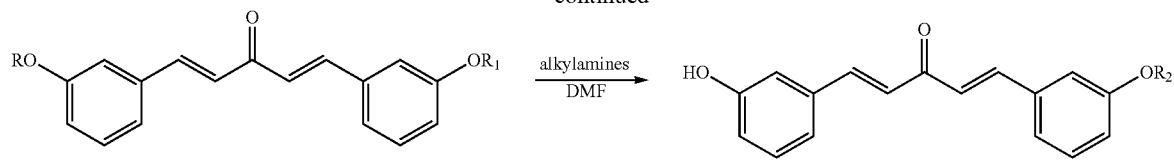
Compound 52: R, R$_1$ = (CH$_2$)$_3$CH$_3$
Compound 54: R = H, R$_1$ = (CH$_2$)$_3$CH$_3$
Compound 58: R = H, R$_1$ = (CH$_2$)$_2$Cl,
Compound 55: R$_2$ = (CH$_2$)$_3$N(C$_2$H$_5$)$_2$
Compound 56: R$_2$ =
Compound 57: R$_2$ =
Compound 59: R$_2$ =
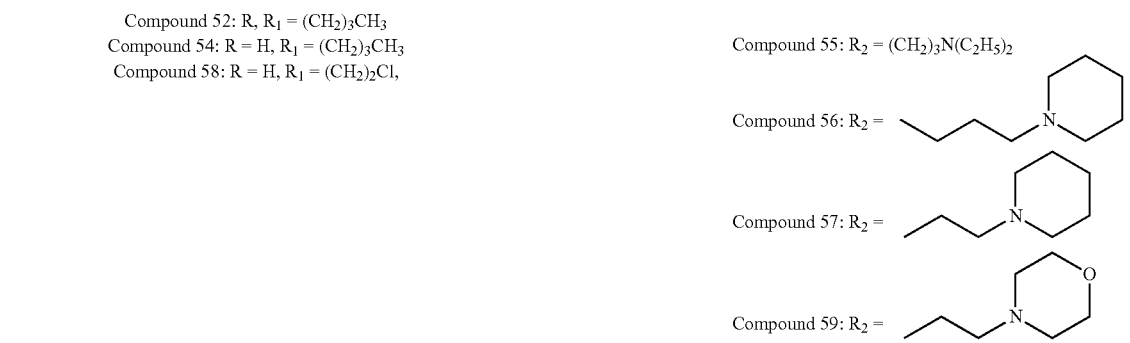
Compound 16
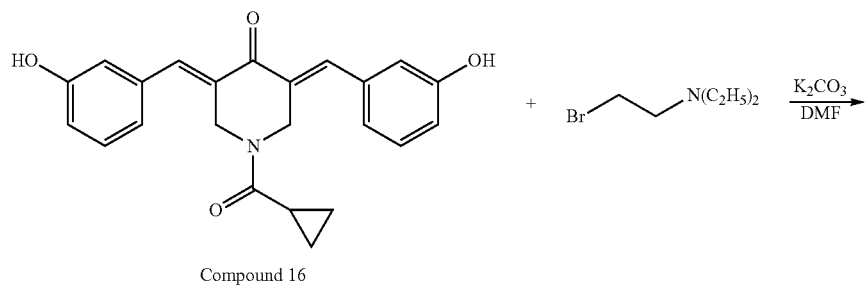
Compound 45: R$_1$ = OH, R$_2$ = O(CH$_2$)$_2$N(C$_2$H$_5$)$_2$
Compound 46: R$_1$ = R$_2$ = O(CH$_2$)$_2$N(C$_2$H$_5$)$_2$H$_2$)$_2$
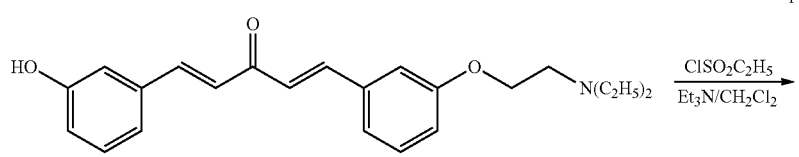
Compound 19
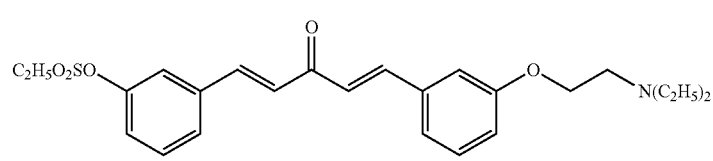
Compound 48
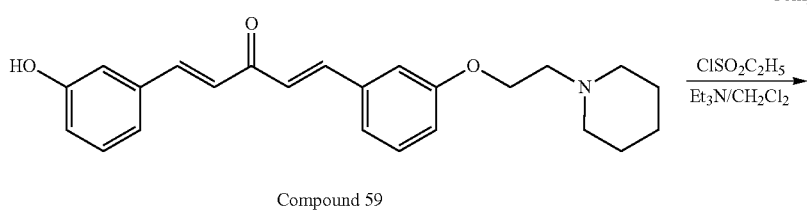
Compound 59

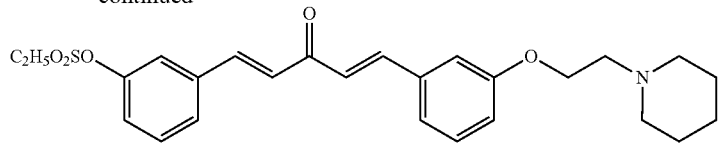

Compound 76

Compounds 19, 35, 36, 67, 68, 71, and 72 were prepared from 1,5-bis-(3-hydroxy-phenyl)-penta-1,4-dien-3-one or Compounds 20 and 62-64 (Scheme 8). (2-Bromo-ethyl)-diethyl-amine hydrobromide (1 eq.) in DMF in the presence of $K_2CO_3$ (2.5 eq.) was used to prepare Compound 19. The reaction mixture was stirred at room temperature for 24 hours. The solid was filtered out and the filtrate was concentrated. The resulting residue was diluted with $CH_2Cl_2$ and washed with water twice. The aqueous layer was extracted with $CH_2Cl_2$ twice and dried over $Na_2SO_4$. After purification by a CombiFlash chromatography system using Grace silica gel cartridge and $CH_2Cl_2$/MeOH, Compound 19 was obtained.

Compound 19: amorphous; ESI MS m/z: 366.30 [M+H]$^+$; $^1$H NMR (300 MHz, CD$_3$OD) δ: 7.74 (d, 1H, J=15.9 Hz, H-1), 7.73 (d, 1H, J=15.9 Hz, H-5), 7.39-7.12 (m, 7H, aromatic H), 7.22 (d, 1H, J=15.9 Hz, H-2), 7.17 (d, 1H, J=15.9 Hz, H-4), 7.63-7.02 and 6.89-6.84 (m, 1H, aromatic H), 4.25 (t, 2H, J=5.4 Hz, OCH$_2$CH$_2$N(CH$_2$CH$_3$)$_2$), 3.17 (t, 2H, J=5.4 Hz, OCH$_2$CH$_2$N(CH$_2$CH$_3$)$_2$), 2.93 (q, 4H, J=7.2 Hz, OCH$_2$CH$_2$N(CH$_2$CH$_3$)$_2$), 1.21 (t, 6H, J=7.2 Hz, OCH$_2$CH$_2$N(CH$_2$CH$_3$)$_2$).

Compound 35: ESI MS m/z: 382.75 [M+H]$^+$; $^1$H NMR (400 MHz, CD$_3$OD) δ: 8.03 (d, 1H, J=16.0 Hz, H-1), 7.34 (d, 1H, J=16.0 Hz, H-5), 7.17 (d, 1H, J=16.0 Hz, H-4), 7.10 (d, 1H, J=16.0 Hz, H-2), 7.23-7.07 (m, 4H, aromatic H), 6.98 (t, 1H, J=8.0 Hz, aromatic H), 6.87 (dd, 1H, J=1.6, 8.4 Hz, aromatic H), 6.83 (dd, 1H, J=2.0, 8.4 Hz, aromatic H), 4.03 (t, 2H, J=4.8, 9.6 Hz, OCH$_2$CH$_2$N(CH$_2$CH$_3$)$_2$), 2.85 (t, 2H, J=4.8, 9.6 Hz, OCH$_2$CH$_2$N(CH$_2$CH$_3$,)$_2$), 2.74 (q, 4H, J=7.2 Hz, OCH$_2$CH$_2$N(CH$_2$CH$_3$)$_2$), 1.13 (t, 6H, J=7.2 Hz, OCH$_2$CH$_2$N(CH$_2$CH$_3$)$_2$).

Compound 36: ESI MS m/z: 481.28 [M+H]$^+$; $^1$H NMR (400 MHz, CD$_3$OD) δ: 8.04 (d, 1H, J=16.0 Hz, H-1), 7.74 (d, 1H, J=16.0 Hz, H-5), 7.25-7.15 (m, 6H, aromatic H, and H-4, 2), 7.02-6.95 (m, 2H, aromatic H), 6.89-6.85 (m, 1H, aromatic H), 4.20 (dd, 2H, J=5.2, 4.8 Hz, OCH$_2$CH$_2$N(CH$_2$CH$_3$)$_2$), 4.05 (dd, 2H, J=5.2, 4.8 Hz, OCH$_2$CH$_2$N(CH$_2$CH$_3$)$_2$), 3.10 (dd, 2H, J=4.8, 4.4 Hz, OCH$_2$CH$_2$N(CH$_2$CH$_3$,)$_2$), 2.92 (dd, 2H, J=4.8, 4.4 Hz, OCH$_2$CH$_2$N(CH$_2$CH$_3$)$_2$), 2.66 (m, 8H, OCH$_2$CH$_2$N(CH$_2$CH$_3$)$_2$), 1.13 (m, 12H, OCH$_2$CH$_2$N(CH$_2$CH$_3$)$_2$).

Compound 67: Amorphous, ESI MS m/z: 394.2 [M+H]$^+$; $^1$H NMR (400 MHz, CD$_3$OD) δ: 7.67 (d, 2H, J=15.6 Hz, H-1,5), 7.51-7.36 (m, 4H, aromatic ring H), 7.08-6.70 (m, 4H, H-2,4 and aromatic ring H), 4.15 (t, 2H, J=5.2, Hz, OCH$_2$CH$_2$N(CH$_2$CH$_3$)$_2$), 2.99 (t, 2H, J=5.2, Hz, OCH$_2$CH$_2$N(CH$_2$CH$_3$)$_2$), 2.73-2.71 (m, 4H, OCH$_2$CH$_2$N(CH$_2$CH$_3$)$_2$), 2.23 (s, 3H, CH$_3$), 2.23-2.17 (m, 3H, CH$_3$), 1.13-1.09 (m, 6H, OCH$_2$CH$_2$N(CH$_2$CH$_3$)$_2$).

Compound 68: Amorphous; ESI MS m/z: 408.1 [M+H]$^+$; $^1$H NMR (400 MHz, CD$_3$OD) δ: 7.68 (d, 2H, J=15.2 Hz, H-1,5), 7.52-7.44 (m, 4H, aromatic ring H), 7.07 (dd, 2H, J=15.2, 4.8 Hz, H-2,4), 6.96-6.92 (m, 2H, aromatic ring H), 4.18 (t, 2H, J=4.8, Hz, OCH$_2$CH$_2$N(CH$_2$CH$_3$)$_2$), 3.85 (s, 3H, OCH$_3$), 3.08 (t, 2H, J=5.2, Hz, OCH$_2$CH$_2$N(CH$_2$CH$_3$)$_2$), 2.80 (m, 4H, OCH$_2$CH$_2$N(CH$_2$CH$_3$,)$_2$), 2.24 (s, 3H, CH$_3$), 2.20 (s, 3H, CH$_3$), 1.14 (t, 6H, J=6.8, Hz, OCH$_2$CH$_2$N(CH$_2$CH$_3$)$_2$).

Compound 71: light brownish solid, ESI MS m/z: 408.1 [M+H]$^+$; $^1$H NMR (400 MHz, CD$_3$OD) δ: 8.03 (d, 2H, J=16.0 Hz, H-1,5), 7.74 (d, 2H, J=9.2 Hz, aromatic ring H), 7.07 (d, 2H, J=16.0, H-2,4), 6.81-6.75 (m, 3H, aromatic ring H), 6.64 (br, 1H, aromatic ring H), 4.11 (t, 2H, J=5.6, Hz, OCH$_2$CH$_2$N(CH$_2$CH$_3$)$_2$), 3.80 (s, 3H, OCH$_3$), 2.90 (t, 2H, J=5.6, Hz, OCH$_2$CH$_2$N(CH$_2$CH$_3$)$_2$), 2.66 (m, 4H, OCH$_2$CH$_2$N(CH$_2$CH$_3$,)$_2$), 2.45 (s, 6H, CH$_3$), 1.08 (t, 6H, J=7.2, Hz, OCH$_2$CH$_2$N(CH$_2$CH$_3$)$_2$).

Compound 72: yellowish solid, ESI MS m/z: 394.1 [M+H]$^+$; $^1$H NMR (400 MHz, CD$_3$OD) δ: 8.02 (dd, 2H, J=15.6, 4.8 Hz, H-1,5), 7.74-7.65 (m, 2H, aromatic ring H), 7.03 (d, 1H, J=15.6 Hz, H-2), 7.99 (d, 1H, J=15.6 Hz, H-4), 6.81 (br, 2H, aromatic ring H), 6.66-6.65 (m, 2H, aromatic ring H), 4.13 (t, 2H, J=5.6, Hz, OCH$_2$CH$_2$N(CH$_2$CH$_3$)$_2$), 2.94 (t, 2H, J=5.5, Hz, OCH$_2$CH$_2$N(CH$_2$CH$_3$)$_2$), 2.73-2.66 (m, 4H, OCH$_2$CH$_2$N(CH$_2$CH$_3$)$_2$), 2.45 (s, 3H, CH$_3$), 2.40 (s, 3H, CH$_3$), 1.11-1.04 (m, 6H, OCH$_2$CH$_2$N(CH$_2$CH$_3$)$_2$).

Compounds 52, 54, and 58 were derived from 1,5-bis-(3-hydroxy-phenyl)-penta-1,4-dien-3-one (synthesized by the method shown in Scheme 4) by reacting with 1-bromobutane (3.0 eq. and 1.2 eq. for compounds 52 and 54, respectively) or 1-bromo-3-chloropropane (1.2 eq. for compound 58) in DMF in the presence of potassium bicarbonate. The reaction mixture was stirred at room temperature (for compounds 52 and 58) or at 80° C. (for compound 58) overnight or with TLC monitoring. The solvent was evaporated under reduced pressure and the residue was partitioned in ethyl acetate and water. The organic layer was washed with water twice and the aqueous washings were extracted with ethyl acetate twice. After dried over Na$_2$SO$_4$, filtered, and concentrated, the oily crude was purified by Combiflash system using n-hexane/ethyl acetate eluent to give desired compounds 52, 54, and 58.

Compound 52: yellow crystalline solid; ESI MS m/z: 379.17 [M+H]$^+$; $^1$H NMR (400 MHz, CDCl$_3$) δ: 7.61 (d, 2H, J=16.0 Hz, H-1,5), 7.30-7.26 (m, 2H, aromatic ring H), 7.16-7.15 (m, 2H, aromatic ring H), 7.10 (br, 2H, aromatic ring H), 7.02 (dd, 2H, J=16.0, 2.0 Hz, H-2,4), 6.93-6.91 (m, 2H, aromatic ring H), 3.97 (t, 4H, J=6.8 Hz, —OCH$_2$CH$_2$CH$_2$CH$_3$), 1.79-1.72 (m, 4H, OCH$_2$CH$_2$CH$_2$CH$_3$), 1.51-1.45 (m, 4H, OCH$_2$CH$_2$CH$_2$CH$_3$), 0.98-0.94 (m, 6H, OCH$_2$CH$_2$CH$_2$CH$_3$).

Compound 54: yellowish solid; ESI MS m/z: 323.08 [M+H]$^+$; $^1$H NMR (400 MHz, CD$_3$OD) δ: 7.68 (dd, 2H, J=15.6, 4.4 Hz, H-1,5), 7.32-7.24 (m, 4H, aromatic ring H), 7.18-7.16 (m, 2H, aromatic ring H), 7.11 (br, 2H, aromatic ring H), 7.04 (dd, 2H, J=15.6, 4.0 Hz, H-2,4), 6.95-6.88 (m, 2H, aromatic ring H), 3.99 (t, 2H, J=12.8, 6.8 Hz, OCH$_2$CH$_2$CH$_2$CH$_3$), 1.81-1.74 (m, 2H, OCH$_2$CH$_2$CH$_2$CH$_3$), 1.53-1.47 (m, 2H, OCH$_2$CH$_2$CH$_2$CH$_3$), 0.99-0.96 (m, 3H, OCH$_2$CH$_2$CH$_2$CH$_3$).

Compound 58: light yellow solid; ESI MS m/z: 329.12 [M+H]$^+$; $^1$H NMR (400 MHz, CDCl$_3$) δ: 7.67 (d, 2H, J=16.0 Hz, H-1,5), 7.34-7.23 (m, 2H, aromatic H), 7.22 (d, 1H, J=8.0

Hz, aromatic ring H), 7.16 (d, 1H, J=8.0 Hz, aromatic ring H), 7.13 (t, 1H, J=2.4 Hz, aromatic ring H), 7.11 (t, 1H, J=2.0 Hz, aromatic ring H), 7.03 (dd, 2H, J=16.0, 2.4 Hz, H-2,4), 6.97-6.94 (m, 1H, aromatic ring H), 6.91-6.88 (m, 1H, aromatic ring H), 4.26 (t, 2H, J=6.0 Hz, —OC$\underline{H_2}$CH$_2$Cl), 3.82 (t, 2H, J=6.0 Hz, —OCH$_2$C$\underline{H_2}$Cl).

Compounds 55-57 and 59 were derived from the compound 58 (for compounds 57 and 59) or the analogues of compound 58, in which the R$_1$ group was replaced with a 3-chloropropoxy (Scheme 8). To a solution of compound 58 in DMF was added piperidine (~4 eq). The resulting reaction mixture was heated to 80° C. and stirred overnight. After cooled to room temperature, the solvent was evaporated under reduced pressure and the residue was partitioned in ethyl acetate and water. The organic phase was washed with water twice and the aqueous washings were extracted with ethyl acetate twice. After dried over Na$_2$SO$_4$, filtered, and concentrated, the crude was purified by a Combiflash system using methylene chloride/methanol eluent, then crystallized from methanol to give compound 57. Amorphous, ESI MS m/z: 378.25 [M+H]$^+$; $^1$H NMR (400 MHz, CD$_3$OD) δ: 7.60 (d, 1H, J=16.0 Hz, H-1), 7.57 (d, 1H, J=16.0 Hz, H-5), 7.27-7.22 (m, 2H, aromatic ring H), 7.15-7.11 (m, 2H, aromatic ring H), 7.02 (t, 1H, J=2.0 Hz, aromatic ring H), 6.97 (d, 1H, J=16.0 Hz, H-2), 6.92 (d, 1H, J=16.0 Hz, H-4), 6.88-6.84 (m, 3H, aromatic ring H), 4.13 (t, 2H, J=5.6 Hz, OC$\underline{H_2}$CH$_2$N(CH$_2$CH$_2$)$_2$CH$_2$), 2.82 (t, 2H, J=5.6 Hz, OCH$_2$C$\underline{H_2}$N(CH$_2$CH$_2$)$_2$CH$_2$), 2.58 (br, 4H, OCH$_2$CH$_2$N(C$\underline{H_2}$CH$_2$,)$_2$CH$_2$), 1.68-1.63 (m, 4H, OCH$_2$CH$_2$N(CH$_2$C$\underline{H_2}$)$_2$CH$_2$), 1.48-1.45 (m, 2H, OCH$_2$CH$_2$N(CH$_2$CH$_2$,)$_2$C$\underline{H_2}$).

Compound 55 was synthesized in the same manner as described above by reaction of 3-chloropropoxy substituted 1,5-bis-(3-substituted-phenyl)-penta-1,4-dien-3-one with diethylamine. Yield: 40%, amorphous, ESI MS m/z: 380.25 [M+H]$^+$; $^1$H NMR (400 MHz, CD$_3$OD) δ: 7.72 (d, 1H, J=16.0 Hz, H-1), 7.71 (d, 1H, J=16.0 Hz, H-5), 7.35-7.25 (m, 4H, aromatic ring H), 7.23-7.21 (m, 1H, aromatic ring H), 7.15 (d, 2H, J=16.0 Hz, H-2,4), 7.10 (t, 1H, J=2.0 Hz, aromatic ring H), 7.01-6.98 (m, 1H, aromatic ring H), 6.86-6.83 (m, 1H, aromatic ring H), 4.11 (t, 2H, J=6.4, Hz, OC$\underline{H_2}$CH$_2$CH$_2$N(CH$_2$CH$_3$)$_2$), 2.99-2.95 (m, 2H, OCH$_2$CH$_2$C$\underline{H_2}$N(CH$_2$CH$_3$)$_2$), 2.88 (q, 4H, J=7.2 Hz, OCH$_2$CH$_2$CH$_2$N(C$\underline{H_2}$CH$_3$)$_2$), 2.10-2.03 (m, 2H, OCH$_2$C$\underline{H_2}$CH$_2$N(CH$_2$CH$_3$)$_2$), 1.18 (t, 6H, J=7.2 Hz, OCH$_2$CH$_2$CH$_2$N(CH$_2$C$\underline{H_3}$)$_2$).

Compound 56 was synthesized in the same manner as described above by reaction of 3-chloropropoxy substituted 1,5-bis-(3-substituted-phenyl)-penta-1,4-dien-3-one with piperidine. Amorphous. ESI MS m/z: 392.25 [M+H]$^+$; $^1$H NMR (400 MHz, CD$_3$OD) δ: 7.72 (d, 1H, J=16.0 Hz, H-1), 7.70 (d, 1H, J=16.0 Hz, H-5), 7.34-7.21 (m, 4H, aromatic ring H), 7.23 (d, 1H, J=16.0 Hz, H-2), 7.15 (d, 1H, J=16.0 Hz, H-4), 7.16-7.15 (m, 1H, aromatic ring H), 7.09 (t, 1H, J=2.4 Hz, aromatic ring H), 6.99-6.96 (m, 1H, aromatic ring H), 6.86-6.83 (m, 1H, aromatic ring H), 4.06 (t, 2H, J=6.4 Hz, —OC$\underline{H_2}$CH$_2$CH$_2$N(CH$_2$CH$_2$)$_2$CH$_2$), 2.62-2.54 (m, 6H, —OCH$_2$CH$_2$C$\underline{H_2}$N(C$\underline{H_2}$CH$_2$)$_2$CH$_2$), 2.05-1.98 (m, 2H, OCH$_2$C$\underline{H_2}$CH$_2$N(CH$_2$CH$_2$)$_2$CH$_2$), 1.66-1.61 (m, 4H, OCH$_2$CH$_2$CH$_2$N(CH$_2$C$\underline{H_2}$)$_2$CH$_2$), 1.51-1.49 (m, 2H, OCH$_2$CH$_2$CH$_2$N(CH$_2$CH$_2$,)$_2$C$\underline{H_2}$).

Compound 59 was synthesized in the same manner as described above by reaction of compound 58 with piperidine. Yield: 35%, amorphous, ESI MS m/z: 380.25 [M+H]$^+$; $^1$H NMR (400 MHz, CD$_3$OD) δ: 7.72 (d, 1H, J=16.0 Hz, H-1), 7.70 (d, 1H, J=16.0 Hz, H-5), 7.35-7.21 (m, 5H, aromatic ring H), 7.14 (d, 2H, J=16.0 Hz, H-2,4), 7.09 (t, 1H, J=2.0 Hz, aromatic ring H), 7.02-6.99 (m, 1H, aromatic ring H), 6.86-6.83 (m, 1H, aromatic ring H), 4.19 (t, 2H, J=5.6 Hz, OC$\underline{H_2}$CH$_2$N(CH$_2$CH$_2$)$_2$O), 3.71 (t, 4H, J=4.8 Hz, OCH$_2$CH$_2$N(CH$_2$C$\underline{H_2}$)$_2$O), 2.84-2.81 (m, 2H, OCH$_2$C$\underline{H_2}$N(CH$_2$CH$_2$)$_2$O), 2.61 (t, 4H, J=4.8 Hz, OCH$_2$CH$_2$N(OC$\underline{H_2}$CH$_2$,)$_2$O).

Compound 45 was synthesized by reacting Compound 16 with 1 eq. of (2-bromo-ethyl)-diethyl-amine hydrobromide in DMF in the presence of K$_2$CO$_3$ (2.5 eq) (Scheme 7). The reaction mixture was stirred at room temperature overnight or with TLC monitoring. The solvent was evaporated under reduced pressure and the residue was partitioned in methylene chloride and water. The organic phase was washed with water three times (or to pH~6-7) and the aqueous washings were extracted with methylene chloride twice. After dried over Na$_2$SO$_4$, filtered, and concentrated, the oily crude was purified by Combiflash system using methylene chloride/methanol eluent to give the desired product as a yellow solid. ESI MS m/z: 475.13 [M+H]$^+$; $^1$H NMR (400 MHz, CD$_3$OD) δ: 7.75 (d, 1H, J=11.6 Hz, benzylidene C$\underline{H}$=), 7.38 (s, br, benzylidene C$\underline{H}$=), 7.28 (s, br, 1H, aromatic ring H), 7.11-6.84 (m, 7H, aromatic ring H), 5.04 (s, 2H, piperidin-4-one), 4.91 (s, 2H, piperidin-4-one), 4.21 (m, 2H, OC$\underline{H_2}$CH$_2$N(CH$_2$CH$_3$)$_2$), 3.14 (m, 2H, OCH$_2$C$\underline{H_2}$N(CH$_2$CH$_3$,)$_2$), 2.87 (m, 4H, OCH$_2$CH$_2$N(C$\underline{H_2}$CH$_3$)$_2$), 1.17 (m, 6H, OCH$_2$CH$_2$N(CH$_2$C$\underline{H_3}$)$_2$), 0.87 (m, 1H, cyclopropanecarbonyl C$\underline{H}$), 0.74 (m, 2H, cyclopropanecarbonyl C$\underline{H_2}$), 0.62 (m, 2H, cyclopropanecarbonyl C$\underline{H_2}$).

Compound 46 was synthesized in the same manner as described above except that 2 eq. (2-bromo-ethyl)-diethylamine hydrobromide and 5 eq. of K$_2$CO$_3$ were used.

Compound 46: a yellow solid; ESI MS m/z: 574.21 [M+H]$^+$; $^1$H NMR (400 MHz, CD$_3$OD) δ: 7.75 (d, 1H, J=11.6 Hz, benzylidene C$\underline{H}$=), 7.38 (s, br, 1H, benzylidene C$\underline{H}$=), 7.28 (s, br, 1H, aromatic ring H), 7.11-6.84 (m, 7H, aromatic ring H), 5.05 (s, 2H, piperidin-4-one), 4.91 (s, 2H, piperidin-4-one), 4.49 (m, 2H, OC$\underline{H_2}$CH$_2$N(CH$_2$CH$_3$)$_2$, 3.86 (m, 2H, OC$\underline{H_2}$CH$_2$N(CH$_2$CH$_3$)$_2$, 3.55 (q, 4H, J=7.6 Hz, OCH$_2$CH$_2$N(C$\underline{H_2}$CH$_3$)$_2$, 3.49 (t, 2H, J=6.4, Hz, OCH$_2$C$\underline{H_2}$N(CH$_2$CH$_3$,)$_2$, 2.87 (t, 2H, J=6.4 Hz, OCH$_2$C$\underline{H_2}$N(CH$_2$CH$_3$,)$_2$, 2.62 (q, 4H, J=7.6 Hz, OCH$_2$CH$_2$N(C$\underline{H_2}$CH$_3$)$_2$, 1.38 (t, 6H, J=7.6 Hz, OCH$_2$CH$_2$N(CH$_2$C$\underline{H_3}$)$_2$, 1.05 (t, J=7.6 Hz, 6H, OCH$_2$CH$_2$N(CH$_2$C$\underline{H_3}$)$_2$, 0.87 (m, 1H, cyclopropanecarbonyl C$\underline{H}$), 0.74 (m, 2H, cyclopropanecarbonyl C$\underline{H_2}$), 0.64 (m, 2H, cyclopropanecarbonyl C$\underline{H_2}$).

Compounds 48 and 76 were synthesized by reacting Compounds 19 and 59, respectively, with ethanesulfonyl chloride (~1.3 eq.) and Et$_3$N (~1.5 eq.) in CH$_2$Cl$_2$ (Scheme 8). The reaction was carried out with stirring at room temperature for 4-5 h. Upon the completion, the reaction mixture was poured into water and washed with water twice. The aqueous layer was extracted with CH$_2$Cl$_2$ twice. After purified with a Combiflash system using CH$_2$Cl$_2$/MeOH eluent, compound 48 was obtained in quantity as light brown solid. ESI MS m/z: 458.21 [M+H]$^+$; $^1$H NMR (400 MHz, CD$_3$OD) δ: 7.72 (d, 1H, J=16.0 Hz, H-1), 7.71 (d, 1H, J=16.0 Hz, H-5), 7.64 (d, 1H, J=7.6 Hz, aromatic ring H), 7.61 (t, 1H, J=2.0 Hz, aromatic ring H), 7.46 (t, 1H, J=8.0 Hz, aromatic ring H), 7.34-7.29 (m, 2H, aromatic ring H), 7.24-7.23 (m, 2H, aromatic ring H), 7.24 (d, 1H, J=16.0 Hz, H-2), 7.19 (d, 1H, J=16.0 Hz, H-4), 6.99-6.97 (m, 1H, aromatic ring H), 4.11 (t, 2H, J=5.6 Hz, OC$\underline{H_2}$CH$_2$N(CH$_2$CH$_3$)$_2$), 3.40 (q, 2H, J=7.6 Hz, SO$_2$C$\underline{H_2}$CH$_3$), 2.91 (t, 2H, J=5.6 Hz, OCH$_2$C$\underline{H_2}$N(CH$_2$CH$_3$)$_2$), 2.67 (q, 4H, J=7.2 Hz, OCH$_2$CH$_2$N(C$\underline{H_2}$CH$_3$,)$_2$), 1.47 (t, 3H, J=7.6 Hz, SO$_2$CH$_2$C$\underline{H_3}$), 1.08 (t, J=7.2 Hz, 6H, OCH$_2$CH$_2$N(CH$_2$C$\underline{H_3}$)$_2$).

Compound 76: amorphous. ESI MS m/z: 470.1 [M+H]$^+$; $^1$H NMR (400 MHz, CDCl$_3$) δ: 7.67 (dd, 2H, J=16.0, 4.4 Hz, H-1,5), 7.54-7.50 (m, 2H, aromatic ring H), 7.43 (t, 1H, J=7.6 Hz, aromatic ring H), 7.32 (m, 2H, aromatic ring H), 7.20-7.15 (m, 2H, aromatic ring H), 7.05 (dd, 2H, J=16.0, 4.4 Hz, H-2,4), 6.95-6.92 (m, 1H, aromatic ring H), 4.30 (t, 2H, J=4.8 Hz, OCH$_2$CH$_2$N(CH$_2$CH$_2$)$_2$CH$_2$), 3.30 (q, 2H, J=7.6 Hz, SO$_2$CH$_2$CH$_3$), 3.01 (t, 2H, J=4.8 Hz, OCH$_2$CH$_2$N(CH$_2$CH$_2$)$_2$CH$_2$), 2.78 (br, 4H, OCH$_2$CH$_2$N(CH$_2$CH$_2$)$_2$CH$_2$), 1.76 (br, 4H, OCH$_2$CH$_2$N(CH$_2$CH$_2$)$_2$CH$_2$), 1.56-1.52 (m, 5H, SO$_2$CH$_2$CH$_3$, and OCH2CH2N(CH$_2$CH$_2$)$_2$CH$_2$).

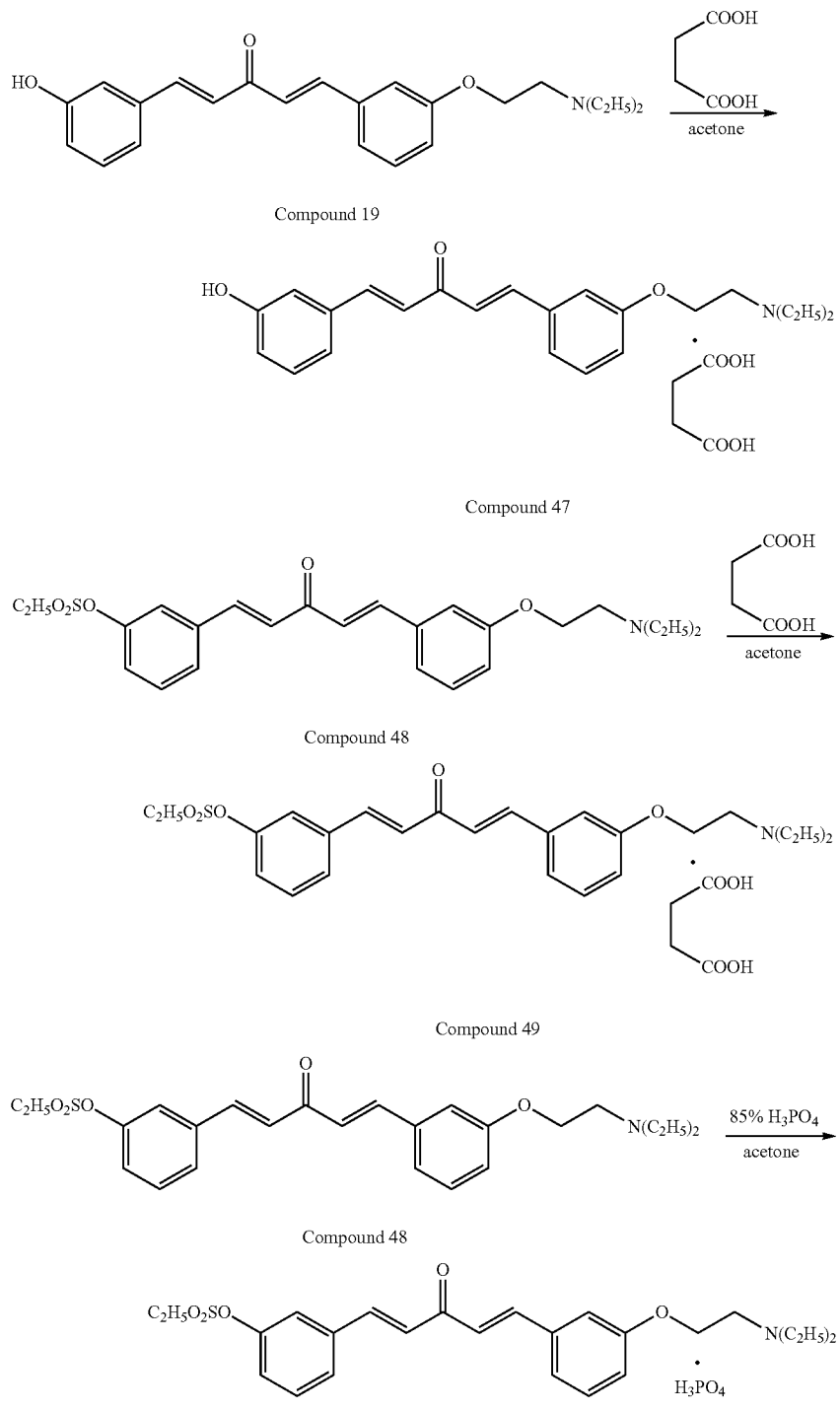

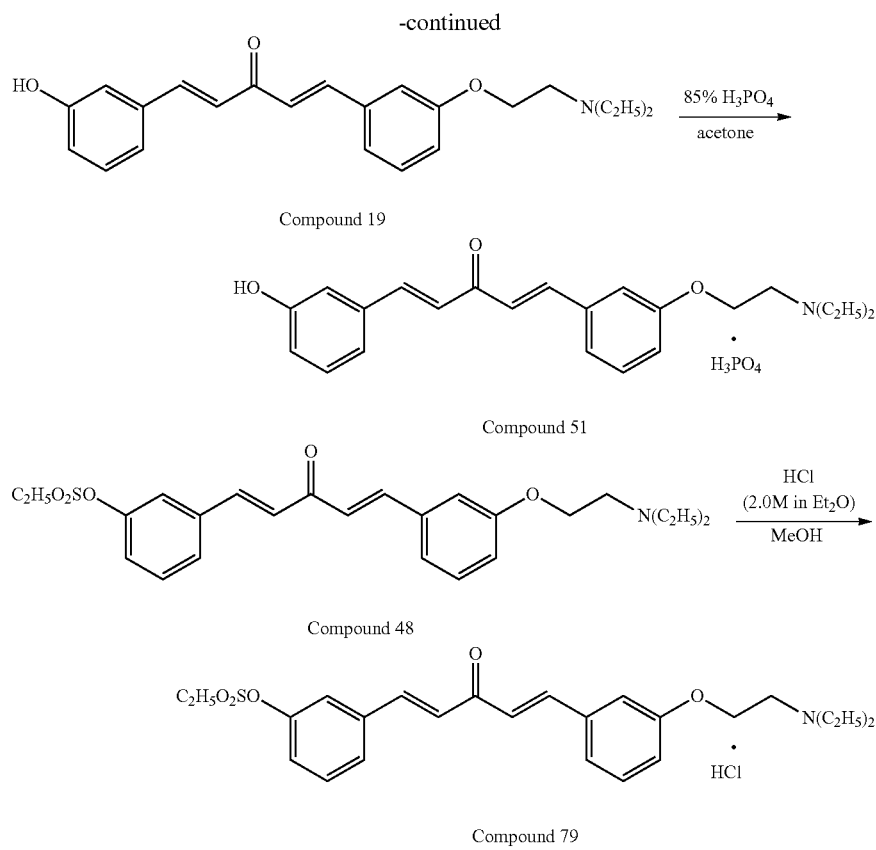

Compound 47 was prepared by reacting compound 19 with succinic acid in acetone. See Scheme 9 above.

To a solution of succinic acid (0.397 g, 3.36 mmol) in acetone (9.5 mL) was added slowly with stirring compound 19 (1.23 g, 3.36 mmol) in 3-4 mL of acetone. During the addition, light yellow crystalline solid was formed and precipitated out. After stirring at room temperature for 2 h, the reaction mixture was stored in a refrigerator overnight. The solid was collected by filtration and washed with acetone to provide compound 47 as a light yellow crystalline solid in 85% yield.

Compound 47: mp. 104-106° C.; ESI MS m/z: 366.30 [M−$C_4H_6O_4$+1]$^+$; $^1$H NMR (400 MHz, $CD_3OD$) δ: 7.72 (d, 1H, J=16.0 Hz, H-1), 7.70 (d, 1H, J=16.0 Hz, H-5), 7.39-7.32 (m, 3H, aromatic H), 7.26 (d, 1H, J=16.0 Hz, H-2), 7.23 (t, 1H, J=8.0 Hz, aromatic H), 7.14 (d, 1H, J=16.0 Hz, H-4), 7.13-7.09 (m, 2H, aromatic H), 7.07-7.04 (m, 1H, aromatic H), 6.86-6.84 (m, 1H, aromatic H), 4.37 (t, 2H, J=5.2 Hz, OC$\underline{H}_2$CH$_2$N(CH$_2$CH$_3$)$_2$, 3.50 (t, 2H, J=5.2 Hz, OCH$_2$C$\underline{H}_2$N(CH$_2$CH$_3$)$_2$, 3.23 (q, 4H, J=7.2 Hz, OCH$_2$CH$_2$N(C$\underline{H}_2$CH$_3$)$_2$, 2.49 (s, 4H, succinic acid —C$\underline{H}_2$C$\underline{H}_2$COOH), 1.32 (t, 6H, J=7.2 Hz, OCH$_2$CH$_2$N(CH$_2$C$\underline{H}_3$)$_2$.

Compound 49 was prepared from Compound 48 in a similar manner. See Scheme 9 above.

Compound 49: brown viscous oil. ESI MS m/z: 458.21 [M−$C_4H_6O_4$+1]$^+$; $^1$H NMR (400 MHz, $CD_3OD$) δ: 7.77 (d, 2H, J=16.0 Hz, H-1,5), 7.67 (d, 1H, J=8.0 Hz, aromatic ring H), 7.65 (t, 1H, J=2.0 Hz, aromatic ring H), 7.51 (t, 1H, J=8.0 Hz, aromatic ring H), 7.38-7.33 (m, 4H, aromatic ring H), 7.30 (d, 1H, J=16.0 Hz, H-2), 7.26 (d, 1H, J=16.0 Hz, H-4), 7.08-7.05 (m, 1H, aromatic ring H), 4.34 (t, 2H, J=5.2 Hz, OC$\underline{H}_2$CH$_2$N(CH$_2$CH$_3$)$_2$, 3.44 (t, 2H, J=5.2 Hz, OCH$_2$C$\underline{H}_2$N(CH$_2$CH$_3$)$_2$, 3.42 (q, 2H, J=7.2 Hz, SO$_2$C$\underline{H}_2$CH$_3$), 3.18 (q, 4H, J=7.2 Hz, OCH$_2$CH$_2$N(C$\underline{H}_2$CH$_3$)$_2$, 2.49 (s, 4H, succinic acid —C$\underline{H}_2$C$\underline{H}_2$COOH), 1.49 (t, 3H, J=7.2 Hz, SO$_2$CH$_2$C$\underline{H}_3$), 1.30 (t, 6H, J=7.2 Hz, OCH$_2$CH$_2$N(CH$_2$C$\underline{H}_3$)$_2$.

Compound 50 was prepared by reacting Compound 48 with phosphoric acid (85% aqueous solution) in acetone. See Scheme 9 above.

To a solution of Compound 48 (0.28 g, 3.36 mmol) in acetone (0.5 mL) was added slowly with stirring a 85% $H_3PO_4$ aqueous solution (1 eq. of $H_3PO_4$, 0.6 mmol) at 0° C. After stirring at room temperature for 1 h, the reaction mixture was stored in a refrigerator overnight. After evaporation of the solvent, the residue was dissolved in 7 mL of $H_2O$ and then frozen. Lyophilization gave Compound 50 as a yellow crystalline solid at the yield of 95%.

Compound 50: ESI MS m/z: 458.21 [M−$H_3PO_4$+1]$^+$; $^1$H NMR (400 MHz, $CD_3OD$) δ: 7.78 (d, 2H, J=16.0 Hz, H-1,5), 7.69 (d, 1H, J=7.6 Hz, aromatic ring H), 7.65 (t, 1H, J=1.6 Hz, aromatic ring H), 7.51 (t, 1H, J=8.0 Hz, aromatic ring H), 7.39-7.35 (m, 4H, aromatic ring H), 7.30 (d, 1H, J=16.0 Hz, H-2), 7.27 (d, 1H, J=16.0 Hz, H-4), 7.11-7.06 (m, 1H, aromatic ring H), 4.43 (t, 2H, J=4.8 Hz, OC$\underline{H}_2$CH$_2$N(CH$_2$CH$_3$)$_2$, 3.60 (t, 2H, J=4.8 Hz, OCH$_2$C$\underline{H}_2$N(CH$_2$CH$_3$)$_2$, 3.42 (q, 2H, J=7.2 Hz, SO$_2$C$\underline{H}_2$CH$_3$), 3.33 (q, 4H, J=7.2 Hz, OCH$_2$CH$_2$N(C$\underline{H}_2$CH$_3$)$_2$, 1.49 (t, 3H, J=7.2 Hz, SO$_2$C$\underline{H}_2$CH$_3$), 1.37 (t, 6H, J=7.2 Hz, OCH$_2$CH$_2$N(C$\underline{H}_2$CH$_3$)$_2$.

Compound 51 was prepared, as a bright yellow crystalline solid, from Compound 19 in a similar manner. See Scheme 9 above.

Compound 51: ESI MS m/z: 366.30 [M−$H_3PO_4$+1]$^+$; $^1$H NMR (400 MHz, $CD_3OD$) δ: 7.74 (d, 1H, J=16.0 Hz, H-1), 7.72 (d, 1H, J=16.0 Hz, H-5), 7.39-7.35 (m, 3H, aromatic H), 7.28 (d, 1H, J=16.0 Hz, H-2), 7.24 (t, 1H, J=7.6 Hz, aromatic H), 7.16 (d, 1H, J=16.0 Hz, H-4), 7.17-7.15 (m, 1H, aromatic H), 7.11-7.06 (m, 2H, aromatic H), 6.87-6.84 (m, 1H, aromatic H), 4.42 (t, 2H, J=4.8 Hz, OC$\underline{H}_2$CH$_2$N(CH$_2$CH$_3$)$_2$, 3.61 (t, 2H, J=4.8 Hz, OCH$_2$C$\underline{H}_2$N(CH$_2$CH$_3$)$_2$, 3.33 (q, 4H, J=7.2 Hz, OCH$_2$CH$_2$N(C$\underline{H}_2$CH$_3$)$_2$, 1.37 (t, 6H, J=7.2 Hz, OCH$_2$CH$_2$N(CH$_2$C$\underline{H}_3$)$_2$.

Compound 79 was prepared as a yellow crystalline solid by reacting Compound 48 with 2.0 M hydrochloride ethyl ether solution.

To a solution of Compound 48 in methanol was added slowly with stirring a 2.0 M hydrochloride ethyl ether solution at 0° C. After stirring at room temperature for 1 h, the reaction mixture was stored in a refrigerator overnight. The solvent was evaporated and the residue was washed with t-buty methyl ether three times. Lyophilization gave Compound 79 as a yellow crystalline solid in quantitative yield.

To a solution of Compound 48 in methanol was added slowly with stirring a 2.0 M hydrochloride ethyl ether solution at 0° C. After stirring at room temperature for 1 h, the reaction mixture was stored in a refrigerator overnight. The solvent was evaporated and the residue was washed with t-buty methyl ether three times. Lyophilization gave Compound 79 as a yellow crystalline solid in quantitative yield. ESI MS m/z: 458.21 [M–HCl+1]$^+$; $^1$H NMR (400 MHz, CD$_3$OD) δ: 7.80 (d, 2H, J=16.0 Hz, H-1,5), 7.71 (d, 1H, J=8.0 Hz, aromatic ring H), 7.67 (t, 1H, J=2.4 Hz, aromatic ring H), 7.53 (t, 1H, J=8.0 Hz, aromatic ring H), 7.42-7.41 (m, 2H, aromatic ring H), 7.39-7.37 (m, 2H, aromatic ring H), 7.32 (d, 1H, J=16.0 Hz, H-2), 7.29 (d, 1H, J=16.0 Hz, H-4), 7.13-7.10 (m, 1H, aromatic ring H), 4.44 (t, 2H, J=4.8 Hz, OC$\underline{H}_2$CH$_2$N(CH$_2$CH$_3$)$_2$, 3.65 (t, 2H, J=4.8 Hz, OCH$_2$C$\underline{H}_2$N(CH$_2$CH$_3$)$_2$, 3.43 (q, 2H, J=7.6 Hz, SO$_2$C$\underline{H}_2$CH$_3$), 3.37 (q, 4H, J=7.2 Hz, OCH$_2$CH$_2$N(C$\underline{H}_2$CH$_3$,)$_2$, 1.51 (t, 3H, J=7.6 Hz, SO$_2$CH$_2$C$\underline{H}_3$), 1.40 (t, 6H, J=7.2 Hz, OCH$_2$CH$_2$N(CH$_2$C$\underline{H}_3$)$_2$.

Syntheses of Compounds 60 and 61

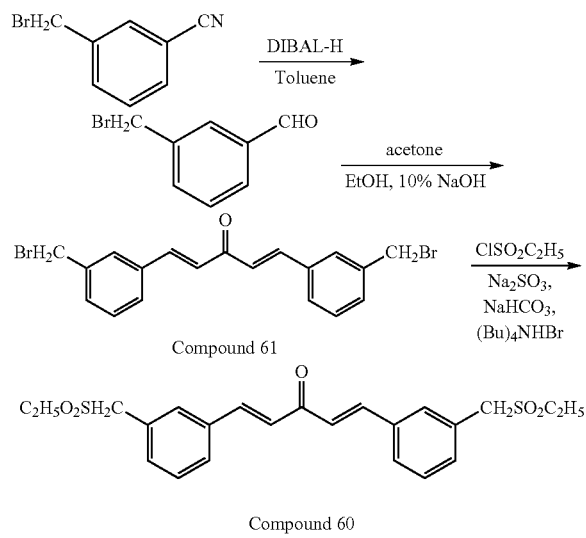

Compounds 60 and 61 were synthesized from α-bromomethyl-tolunitril. To a solution of α-bromomethyl-tolunitril (15.3 mmol) in toluene (30 mL) was added DIBAL-H in THF (1.0 M, 1.4 eq.) at 0° C. within 30 minutes. After stirring at 0° C. for 2 h, the reaction mixture was poured into a mixture of 40 mL of methylene chloride and 100 mL of 10% HCl. The resulting mixture was stirred for 1 h and the organic layer was washed with water and then brine, and the aqueous was extracted with methylene chloride twice. After dried over Na$_2$SO$_4$, filtered, and concentrated, the obtained semi-oily product was stored in a refrigerator to give 3-(bromomethyl) benzaldehyde as a white crystalline solid in quantitative yield. Reaction of the resulting compound with acetone in ethanol following the procedure described in Scheme 4 yielded Compound 61 as a light yellow crystalline solid. ESI MS m/z: 420.9 [M+H]$^+$; $^1$H NMR (400 MHz, CDCl$_3$) δ: 7.71 (d, 2H, J=16.0 Hz, H-1,5), 7.63-7.60 (m, 2H, aromatic ring H), 7.54-7.50 (m, 2H, aromatic ring H), 7.44-7.37 (m, 4H, aromatic ring H), 7.08 (d, 2H, J=16.0 Hz, H-2,4), 4.50 (s, 4H, —C$\underline{H}_2$Br).

Compound 60 was obtained by reacting Compound 61 in CH$_2$Cl$_2$ with a mixture of ethanesulfonyl chloride (2 eq.), sodium sulfite (4 eq.), sodium bicarbonate (4 eq.) in water. The resulting mixture was stirred at 35-36° C. overnight. The reaction mixture was diluted with methylene chloride, washed with water then brine, and dried over Na$_2$SO$_4$. The crude product was purified with a Combiflash system using n-hexanes/EtOAc eluent to afford the desired product as light yellow solid. Yield: 44%. ESI MS m/z: 447.1[M+H]$^+$; $^1$H NMR (400 MHz, CDCl$_3$) δ: 7.55 (d, 2H, J=16.0 Hz, H-1,5), 7.53 (br, 2H, aromatic H), 7.47-7.25 (m, 2H, aromatic ring H), 7.42-7.38 (m, 4H, aromatic ring H), 6.70 (d, 2H, J=16.0 Hz, H-2,4), 4.57 (s, 4H, —C$\underline{H}_2$SO$_2$CH$_2$CH$_3$), 2.82-2.70 (m, 4H, —CH$_2$SO$_2$C$\underline{H}_2$CH$_3$), 1.30 (t, 6H, J=7.2 Hz, —CH$_2$SO$_2$CH$_2$C$\underline{H}_3$), Biological Assays Inhibitory Effects on Proliferation of Human Lernert's T Cell Lymphoma KT-3

Inhibitory effects of compounds of this invention on the growth of human Lennert's T cell lymphoma KT-3 cells, an IL-6-dependent cell line, were determined as described below. Briefly, KT-3 cells were transferred into wells of 96-well plates (2.5×10$^3$/well) and cultured in RPMI-1640 medium (GIBCO) containing penicillin (25 U/ml), streptomycin (25 μg/ml), 10% heat-inactivated fetal bovine serum (FBS), and hIL-6 (2.5 ng/ml, R&D systems). To experimental wells, test compounds at various concentrations (in triplicates) were added immediately after the cells were plated. To the control wells, an equal volume of vehicle, DMSO (0.1% v/v), was added. After incubating the cells with the compounds or in vehicle for 48 hours, cell viability was assessed using a CellTiter Glo Luminescent Cell Viability Assay Kit (Promega, Madison, Wis.). The resultant luminescence was quantified using Microplate Luminometer LB96V (EG&G BERTH HOLD) according to the manufacturer's protocol. The cell surviving rate was calculated by dividing the luminescence value of compound-treated cells with that of vehicle-treated cells.

All of Compounds 1-79 exhibited inhibitory effect on IL-6-induced KT-3 cell proliferation. Some compounds, i.e., Compounds 6, 16, 18, 19, 26, 27, 35, 36, 45-51, 56, 57 and 79 unexpectedly had IC$_{50}$ values (the concentration at which a compound suppresses cell growth by 50%) equal to or even lower than 0.05 μM. In addition, all compounds 1-79 inhibited KT-3 cell proliferation in a dose-dependent manner.

Inhibition of Growth of Various Human Tumor Cell Lines

The inhibitory effects of Compound 6 were determined as described below on the growth of colon cancer cells (HCT116, HT29, SW480, and SW620), colon adenocarcinoma cells (Colo205), prostate adenocarcinoma cells (PC-3 and Du145), prostate carcinoma cells (CWR22RV and LNCap), non-small cell lung carcinoma cells (NCI-H1299), lung adnocarcinoma cells (A549), large cell lung carcinoma cells (NCI-H460), breast metastatic carcinoma cells (MDA-MB-453), breast ductal carcinoma cells (T-47D), breast adnocarcinoma cells (MCF7), hepatocellular carcinoma cells (Huh-7 and HepG2), pancreatic carcinoma cells (PANC-1), cervix adnocarcinoma cells (Hela), IL-6-dependent Lennert's T-cell lymphoma cells (KT-3), IL-6-dependent multiple myeloma cells (INA-6), multiple myeloma cells (KMM-1 and U266), myeloid leukemia cells (HL-60), and T-cell leukemia cells (Jurkat). Briefly, tumor cells were seeded at densities ranging from $1\times10^3$ to $4\times10^3$/well in 96-well Microtest III tissue culture plates (Falcon, N.J.). After cultured in DMEM (GIBCO) containing penicillin (25 units/milliliter), streptomycin (25 micrograms/milliliter), and 10% heat-inactivated FBS for 12 hours, cells were treated with various concentrations ranging from 0 to 5 µM of compound 6 for 72 h. The viability of the tumor cells was then assessed using the tetrazolium-based calorimetric assay (MTT) as described in Su et al., J Mol Cell Cardiol. 1998; 30:587-598. The cells were incubated with the MTT dye (5 mg/mL) at 37° C. for 3 hours. The resultant formazan crystals were solubilized with MTT lysis buffer (50% DMF, 24 mM HCl, 2% Acetic Acid, 5% SDS) and the absorbance at 595 nm was measured using a Benchmark microplate reader (BIO-RAD, Hercules, Calif.). The cells surviving rate was calculated by the absorbance value of compound-treated cells vs. that of vehicle-treated cells.

Compound 6 exhibited dose-dependent inhibitory effects on the growth of all tumor cells tested and with $IC_{50}$ values ranging from 0.02 to 5.5 µM.

Western Blot Analysis of MRG, STAT1, STAT3, and STAT5 Proteins in KT-3 Cells

Western Blot analysis was performed as described in Kawashima et al., J. Immunol. 2001, 167:3652-3660, with minor modifications. Briefly, KT-3 cells were treated with 1, 5, or 20 µM of compound 6 or vehicle alone in the above described IL-6-containing medium. At various time points after incubation (i.e., 0.5, 1, 3, and 6 hours after the treatment), cells were harvested and lysed using a lysis buffer (1.0% Triton X-100, 50 mM Tris-HCl (pH 7.5), 0.1 mM EDTA, 150 mM NaCl, 200 µM $Na_3VO_4$, 50 mM NaF, 1 mM dithiothreitol, 0.4 mM phenylmethylsulfonyl fluoride, 3 µg/ml of aprotinin, 2 µg/ml of pepstatin A, 1 µg/ml of leupeptin) at $2\times10^7$ cells/ml on ice for 30 min. Cell lysates were harvested by centrifugation at 12,000×g for 15 min. The samples ($1\times10^5$ cell equivalent/lane) were subjected to sodium dodecyl sulfate-polyacrylamide gel electrophoresis and subsequently transferred onto Immobilon filters (Millipore). After blocked with 5% BSA, the filter was probed with anti-pSTAT3, STAT3, STAT5, STAT1, MRG or Actin Abs. The rabbit polyclonal anti-STAT3, anti-STAT5, anti-STAT1, and anti-Actin antibodies (Abs), and mouse monoclonal anti-pSTAT3 Ab (B-7) were obtained from Santa Cruz Biotechnology. Affinity purified anti-MRG Ab was prepared as described previously in Hirose et al., J. Biol. Chem. 276: 5821-5828. The filter was further incubated with HRP-conjugated secondary antibodies. Finally, the proteins were visualized using the Enhanced Chemiluminescence (ECL) system (Amersham).

The results show that Compound 6 down-regulated MRG (MgcRacGAP, an evolutionarily conserved GTPase-activating) protein, STAT3, and STAT5 proteins and inhibited phosphorylation of STAT3 protein in KT-3 cells in a time and dose-dependent manner. In contrast, this compound had no effect on the expression of STAT1 in the KT3 cells under the testing condition.

Inhibitory Effect on Human Colon Cancer (HCT-116) in a Mouse Xenograft Model

The in vivo experiments were carried out under an Institutional Animal Care and Use Committee-approved protocol and followed Institutional guidelines for proper and humane use of animals in research. Six-week-old female athymic nude mice were purchased from the Harlan Laboratory. Each of eight mice was injected subcutaneously with $1\times10^6$ HCT-116 cells mixed with Matrigel (BD Bioscience) at the left flank. After injection, tumors were allowed to grow for 5 days into a palpable size (volume ~100 $mm^3$) before treatment. Mice were randomized into two groups (n=4 per group). The control group was injected with a vehicle solution only (i.e., 10% DMSO and 90% corn oil), while the experimental group received a daily injection (i.p.) of compound 6 (at a dose of 40 mg/kg body weight, dissolved in the vehicle solution) from days 0 (the initiation day of injection) to 4 and from days 7 to 10. The sizes of tumors were measured twice a week using a Vernier caliper and calculated using the following formula: length×width×height×0.5236, as described in Rockwell et al., J Natl. Cancer Inst. 1972; 49:735-747.

The result shows that Compound 6 inhibited human colon cancer growth in the xenograft mouse model.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method for treating a signal transduction and transcription (STAT) protein-associated condition, the method comprising administering to a subject in need thereof an effective amount of a compound of formula (I):

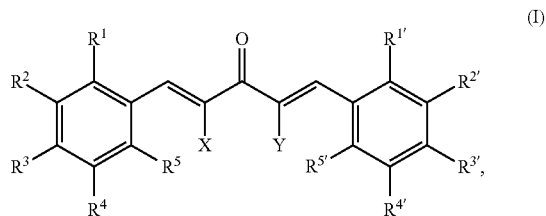

wherein each of X and Y, independently, is H, alkyl, or halo; and each of $R^1$, $R^2$, $R^3$, $R^4$, $R^5$, $R^{1'}$, $R^{2'}$, $R^{3'}$, $R^{4'}$, and $R^{5'}$, independently, is H, alkyl, halo, OH, $R_c$—O—, $R_cS(O)_2$—O—, $(R_d)_2P(O)$—O—, or $(R_dO)_2P(O)$—O—, $R_c$ being unsubstituted alkyl or alkyl substituted with halo, OH, alkoxy, amino, or cycloalkyl, and $R_d$ being H, OH, $C_2$-$C_{10}$ alkyl, or alkoxy; in which at least one of $R^1$, $R^2$, $R^3$, $R^4$, $R^5$, $R^{1'}$, $R^{2'}$, $R^{3'}$, $R^{4'}$, and $R^{5'}$ is $R_dS(O)_2$—O—, $(R_d)_2P(O)$—O—, or $(R_dO)_2P(O)$—O—, and the STAT protein-associated condition is lymphoma lung cancer, breast cancer, pancreatic cancer, cervical cancer, leukemia, or multiple myeloma.

2. The method of claim 1, wherein the STAT protein-associated condition is pancreatic cancer, lung cancer, breast cancer, lymphoma, or leukemia.
3. The method of claim 1, wherein the compound is one of the following compounds:
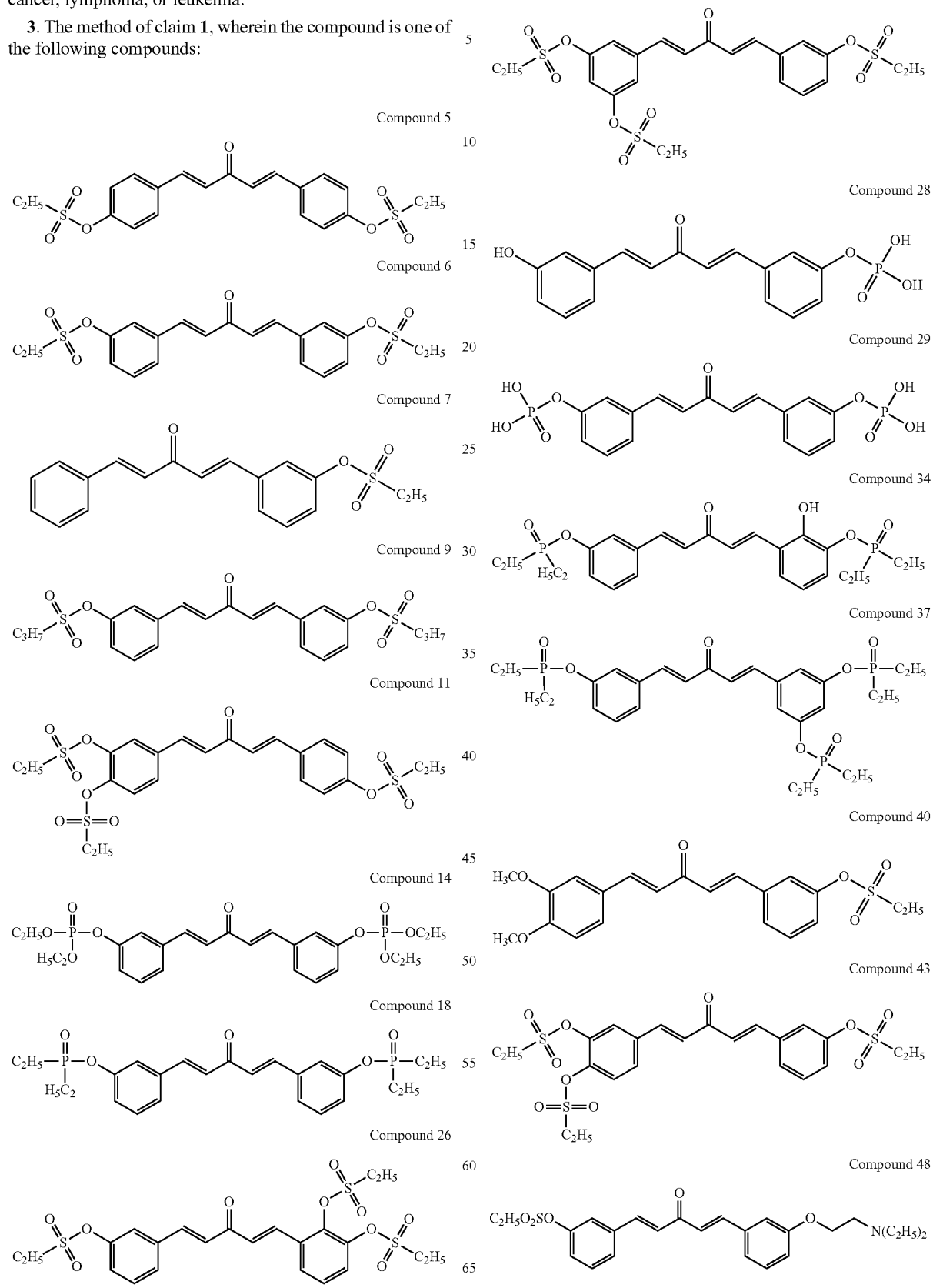

Compound 49

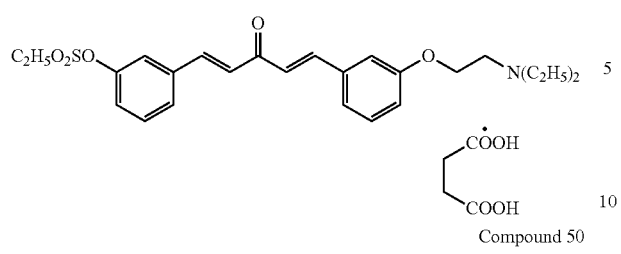

Compound 50

Compound 53

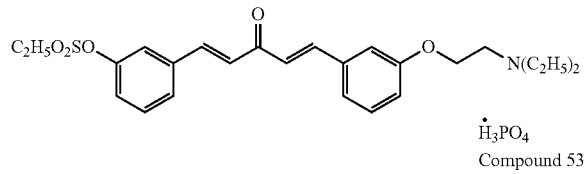

Compound 60

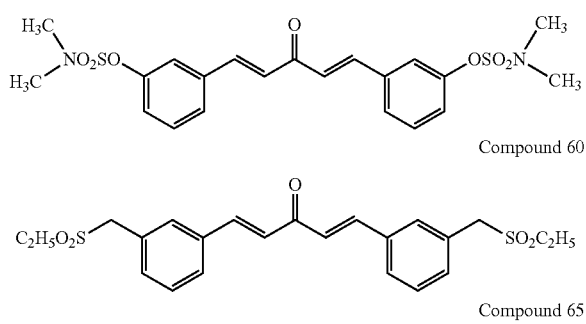

Compound 65

Compound 66

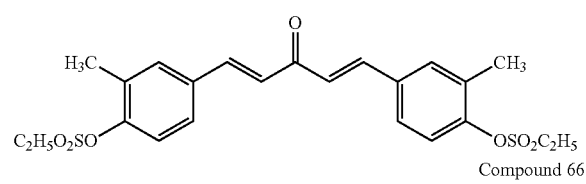

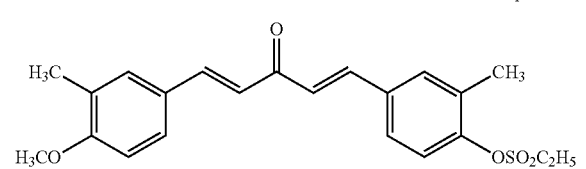

Compound 6

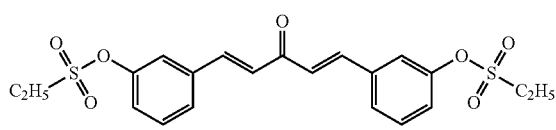

Compound 19

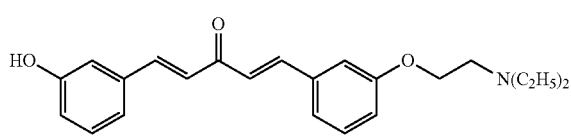

Compound 69

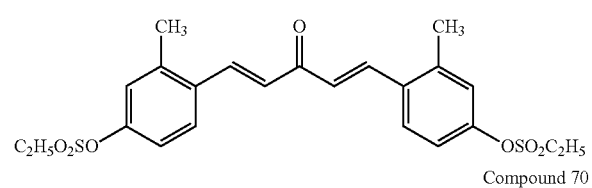

Compound 70

Compound 74

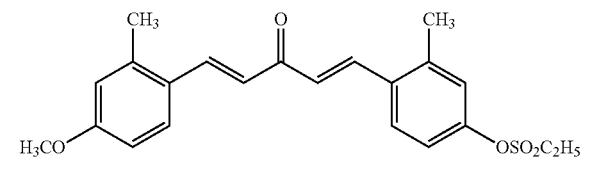

Compound 77

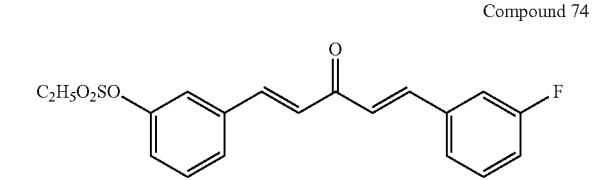

Compound 79

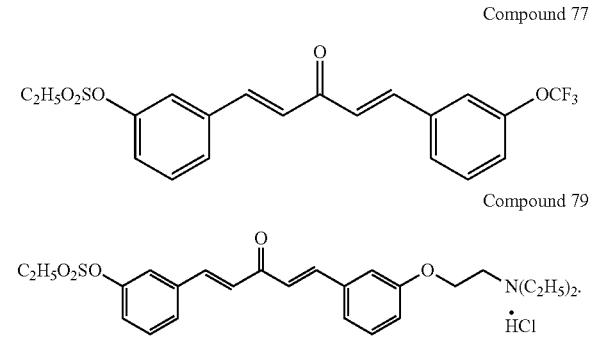

4. The method of claim 3, wherein the STAT protein-associated condition is pancreatic cancer, lung cancer, breast cancer, lymphoma, or leukemia.

5. A method for treating a STAT protein-associated condition, the method comprising administering to a subject in need thereof an effective amount of one of the following compounds:

Compound 18

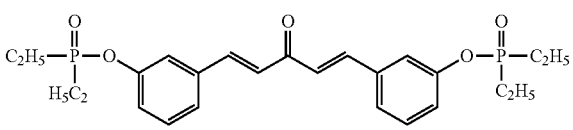

Compound 35

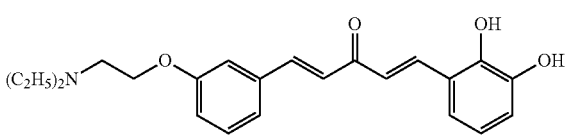

Compound 36

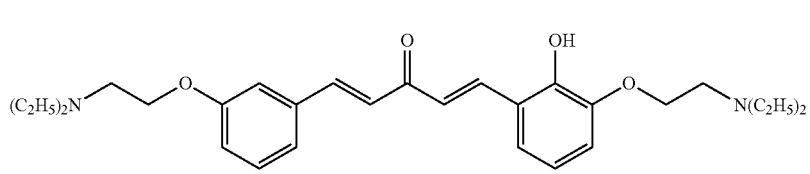

-continued

Compound 47

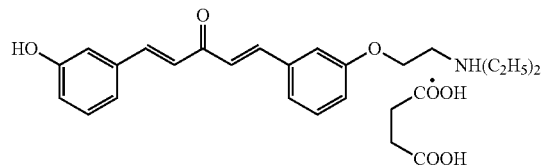

Compound 48

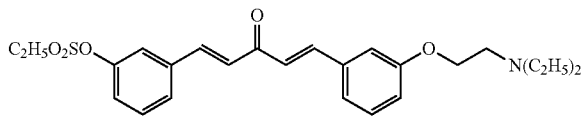

Compound 49

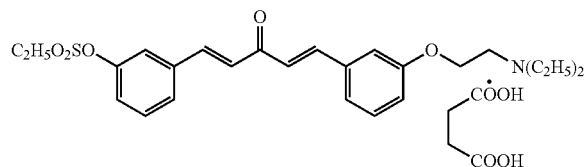

Compound 57

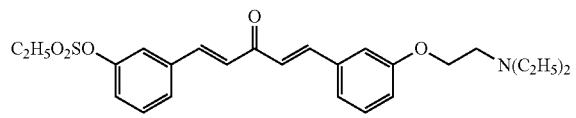

wherein the STAT protein-associated condition is lymphoma, lung cancer, breast cancer, pancreatic cancer, cervical cancer, leukemia, or multiple myeloma.

6. The method of claim 5, wherein the compound is one of the following compounds:

Compound 6

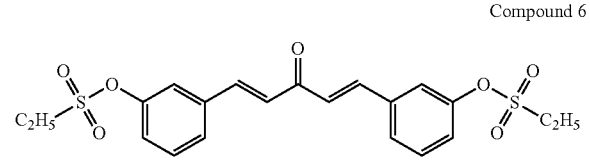

Compound 48

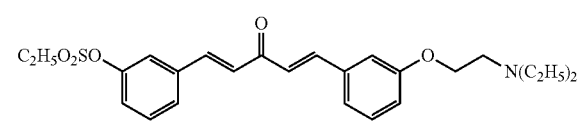

Compound 49

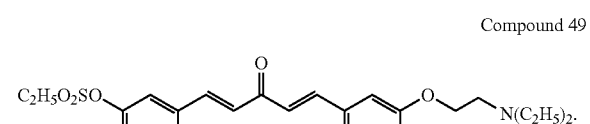

-continued

Compound 48

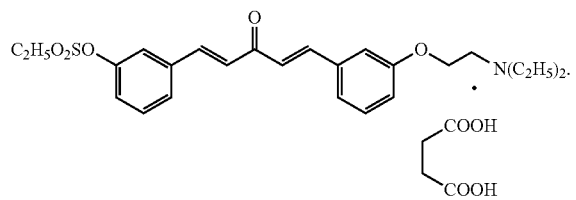

Compound 49

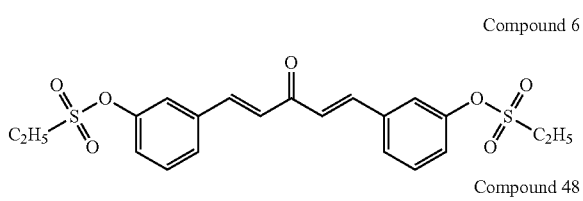

9. The method of claim 5, wherein the STAT protein-associated condition is pancreatic cancer.

10. The method of claim 9, wherein the compound is one of the following compounds:

Compound 6

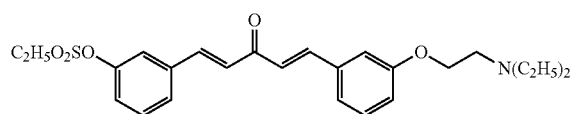

Compound 48

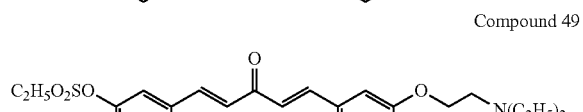

Compound 49

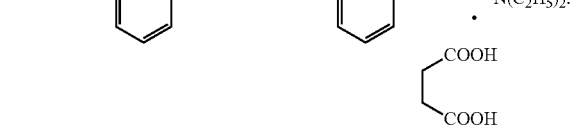

7. The method of claim 5, wherein the STAT protein-associated condition is pancreatic cancer, lung cancer, breast cancer, lymphoma, or leukemia.

8. The method of claim 7, wherein the compound is one of the following compounds:

Compound 6

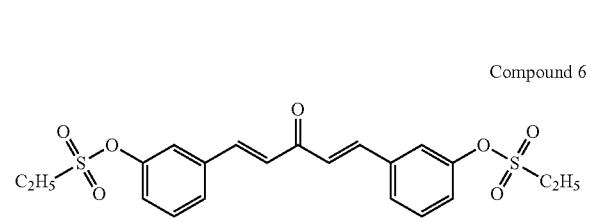

11. The method of claim 5, wherein the STAT protein-associated condition is lung cancer.

12. The method of claim 11, wherein the compound is one of the following compounds:

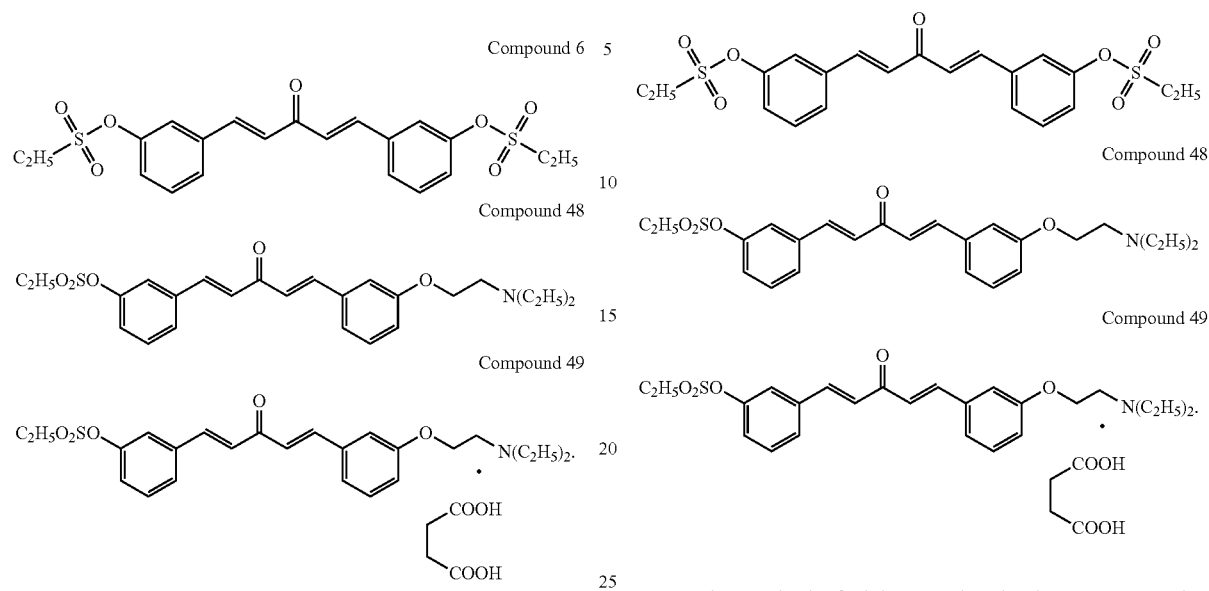

13. The method of claim 5, wherein the STAT protein-associated condition is breast cancer.

14. The method of claim 13, wherein the compound is one of the following compounds:

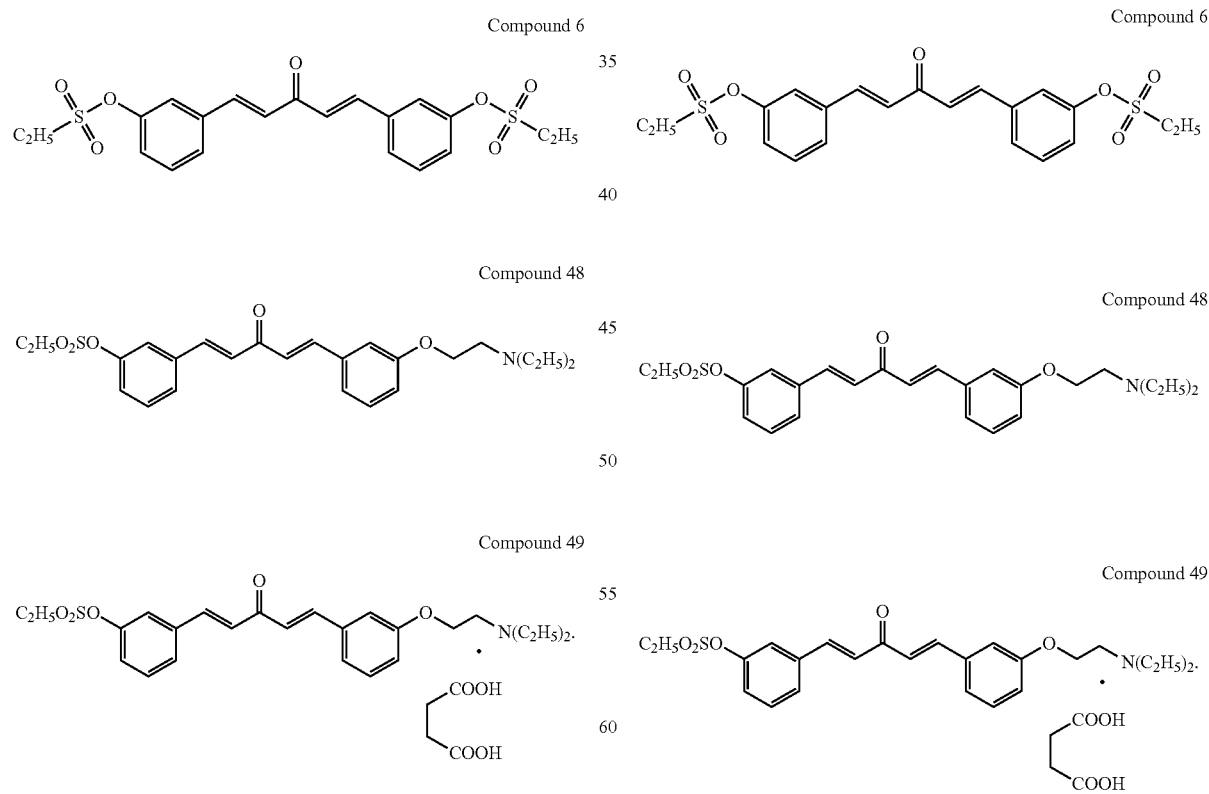

15. The method of claim 5, wherein the STAT protein-associated condition is cervical cancer.

16. The method of claim 15, wherein the compound is one of the following compounds:

17. The method of claim 5, wherein the STAT protein-associated condition is multiple myeloma, lymphoma, or leukemia.

18. The method of claim 17, wherein the compound is one of the following compounds:

19. A method for deactivating a STAT protein, the method comprising contacting the STAT protein with an effective amount of a compound of formula (I):

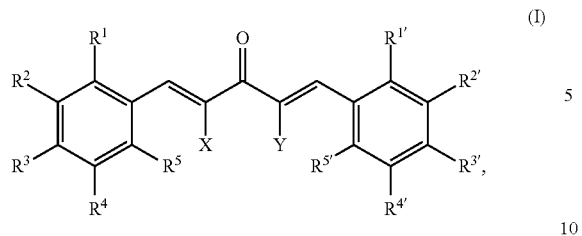

wherein each of X and Y, independently, is H, alkyl, or halo; and each of $R^1$, $R^2$, $R^3$, $R^4$, $R^5$, $R^{1'}$, $R^{2'}$, $R^{3'}$, $R^{4'}$, and $R^{5'}$, independently, is H, alkyl, halo, OH, $R_c$—O—, $R_dS(O)_2$—O—, $(R_d)_2P(O)$—O—, or $(R_dO)_2P(O)$—O—, $R_c$ being unsubstituted alkyl or alkyl substituted with halo, OH, alkoxy, amino, or cycloalkyl, and $R_d$ being H, OH, $C_2$-$C_{10}$ alkyl, or alkoxy; in which at least one of $R^1$, $R^2$, $R^3$, $R^4$, $R^5$, $R^{1'}$, $R^{2'}$, $R^{3'}$, $R^{4'}$, and $R^{5'}$ is $R_dS(O)_2$—O—, $(R_d)_2P(O)$—O—, or $(R_dO)_2P(O)$—O—.

* * * * *